US006180339B1

(12) United States Patent
Sandhu et al.

(10) Patent No.: US 6,180,339 B1
(45) Date of Patent: Jan. 30, 2001

(54) NUCLEIC ACID PROBES FOR THE DETECTION AND IDENTIFICATION OF FUNGI

(75) Inventors: Gurpreet S. Sandhu, Bloomington; Bruce C. Kline, Rochester, both of MN (US)

(73) Assignee: Bayer Corporation, East Walpole, MA (US)

( * ) Notice: Under 35 U.S.C. 154(b), the term of this patent shall be extended for 0 days.

(21) Appl. No.: 08/871,678

(22) Filed: Jun. 6, 1997

Related U.S. Application Data

(63) Continuation-in-part of application No. 08/373,127, filed on Jan. 13, 1995, now Pat. No. 5,763,169, and a continuation-in-part of application No. 08/435,684, filed on May 5, 1995, now Pat. No. 5,707,802.

(51) Int. Cl.[7] .............................. C12Q 1/68; C07H 21/02
(52) U.S. Cl. ................................................. 435/6; 536/23.1
(58) Field of Search ....................... 435/6, 91.2; 536/23.1

(56) References Cited

U.S. PATENT DOCUMENTS

| | | | |
|---|---|---|---|
| 4,358,535 | * 11/1982 | Falkow et al. | 435/5 |
| 4,851,330 | 7/1989 | Kohne | 435/6 |
| 5,288,611 | 2/1994 | Kohne | 435/6 |
| 5,292,874 | 3/1994 | Milliman | 536/24.32 |
| 5,324,632 | 6/1994 | Weisburg et al. | 435/6 |
| 5,352,579 | 10/1994 | Milliman | 435/6 |
| 5,364,759 | 11/1994 | Caskey et al. | 435/6 |
| 5,407,814 | 4/1995 | Pearson et al. | 435/91.2 |
| 5,501,951 | 3/1996 | Milliman | 435/6 |
| 5,503,980 | 4/1996 | Cantor | 435/6 |
| 5,525,464 | 6/1996 | Drmanac et al. | 435/6 |
| 5,580,971 | 12/1996 | Mitsuhashi | 536/24.32 |
| 5,593,841 | 1/1997 | Hogan et al. | 435/6 |

FOREIGN PATENT DOCUMENTS

| | | |
|---|---|---|
| 0272009A2 | 6/1988 | (EP) . |
| 0327390A2 | 8/1989 | (EP) . |
| 0422872A3 | 4/1991 | (EP) . |
| 0438587B1 | 4/1995 | (EP) . |
| 88/03957 | 6/1988 | (WO) . |
| 90/13669 | 11/1990 | (WO) . |
| 95/29260 | 11/1995 | (WO) . |
| 96/21741 | 7/1996 | (WO) . |
| 96/29432 | 9/1996 | (WO) . |

OTHER PUBLICATIONS

Sequence Alignments Comparisons.*
ATCC Catalogue of Filamentous FUNGI, 18th Edition, pp. 50, 112–113 (1991).
Carr, L. G. et al., "Organization of the 5.8S, 16–18S and 23–28S ribosomal RNA genes of *Cephalosporium–acremonium*", *Current Genetics*, vol. 12, pp. 209–214 (1987).
Chomczynski and Sacchi, *Analytical Biochemistry*, vol. 162, pp. 156–159 (1987).

Holmes et al., *Journal of Clinical Microbiology*, vol. 32, pp. 228–231 (1994).
Liu et al., "Sequence and variability of the 5.8S and 26S rRNA genes of *Pneumocystis carinii*," *Nucleic Acids Research*, vol. 20, No. 14: 3763–3772 (1992).
Tang et al., A Single–Tube Nested PCR for *Pneumocystis carinii* f. sp. hominis, *Journal of Clinical Microbiology*, vol. 35, No. 6: 1597–1599 (1997).
Sandhu et al., Molecular Detection and Identification of *Paracoccidioides brasiliensis*, *Journal of Clinical Microbiology*, vol. 35, No. 7: 1894–1896 (1997).
Hopfer et al., *Journal of Medical and Veterinary Mycology*, vol. 31, pp. 65–75 (1993).
Kwon–Chung and Bennett, *Medical Mycology*, Lee and Febiger, 1992.
Leclerc et al., *Journal of Medical and Veterinary Mycology*, vol. 32, pp. 331–341 (1994).
Lott et al., Yeast, vol. 9, pp. 1199–1206 (1993).
Maiwald et al., *Journal of Medical and Veterinary Mycology*, vol. 32, pp. 115–122 (1994).
Makimura et al., *Journal of Medical Microbiology*, vol. 40, pp. 358–364 (1994).
Mitchell et al., *Journal of Clinical Microbiology*, vol. 32, pp. 253–255 (1994).

(List continued on next page.)

*Primary Examiner*—Eggerton A. Campbell
(74) *Attorney, Agent, or Firm*—Weingarten, Schurgin, Gagnebin & Hayes LLP

(57) ABSTRACT

Nucleic acid probes and primers are described for detecting fungi that cause disease in humans and animals, as well as spoilage of food and beverages. These probes can detect rRNA, rDNA or polymerase chain reaction products from a majority of fungi in clinical, environmental or food samples. Nucleic acid hybridization assay probes specific for Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergillus ustus,* Beauveria sp., Bipolaris sp., Blastoschizomyces sp., *Blastomyces dermatitidis, Candida albicans, Candida glabrata, Candida guilliermondii, Candida kefyr, Candida krusei, Candida lusitaniae, Candida parapsilosis, Candida tropicalis,* Chrysosporium sp., Cladosporium sp., *Coccidioides immitis, Cryptococcus neoformans* var gattii serotype B, *Cryptococcus neoformans* serotype A, *Cryptococcus laurentii, Cryptococcus terreus,* Curvularia sp., Fusarium sp., *Filobasidium capsuligenum, Filobasidiella* (Cryptococcus) *neoformans* var bacillispora serotype C, *Filobasidiella* (Cryptococcus) *neoformans* var neoformans serotype D, *Filobasidium uniguttulatum,* Geotrichum sp., *Histoplasma capsulatum,* Malbranchea sp., Mucor sp., Paecilomyces sp., *Paracoccidioides brasiliensis,* Penicillium species, *Pneumocystis carinii, Pseudallescheria boydii,* Rhizopus sp., *Sporothrix schenkii, Scopulariopsis brevicaulis, Scopulariopsis brumpti, Saccharomyces cerevisiae,* and *Trichosporon beigelii* are also described.

13 Claims, 1 Drawing Sheet

OTHER PUBLICATIONS

Moukhamedov R., et al., "Use of Polymerase Chain Reaction–Amplified Ribosomal Intergenic Sequences for the Diagnosis of *Verticillium tricorpus*", *Phytopathology*, vol. 84, pp. 256–259 (1994).

Nakamura et al, Rinsho Byuri—Japanese Jour. of Clinical Pathology, vol. 42, pp. 676–681 (1994).

Neuvéglise C., et al., "Identification of group–I introns in the 28s rDNA of the entomopathogenic fungus *Beauveria brongniartii*", *Current Genetics*, vol. 27, pp. 38–45 (1994).

Sandhu, G. S., et al., "Molecular Probes for Diagnosis of Fungal Infections", *Journal of Clinical Microbiology*, vol. 33, pp. 2913–2919 (1995).

Sarosi and Davies, eds., Fungal Diseases of the Lung, Raven Press, 1993.

Spreadbury et al., *Journal of Clinical Microbiology*, vol. 31, pp. 615–621 (1993).

Stockman et al., *Journal of Clinical Microbiology*, vol. 31, pp. 845–850 (1993).

Vilgalys, R. et al., "Rapid Genetic Identification and Mapping of Enzymatically Amplified Ribosomal DNA from Several Cryptococcus Species", Journal of Bacteriology, vol. 172, No. 8, pp. 4238–4246 (1990).

* cited by examiner

SEQUENCE LISTING (1) GENERAL INFORMATION:

(iii) NUMBER OF SEQUENCES: 80

(2) INFORMATION FOR SEQ ID NO:1:

(i) SEQUENCE CHARACTERISTICS:
      (A) LENGTH: 20
      (B) TYPE: nucleic acid
      (C) STRANDEDNESS: single
      (D) TOPOLOGY: linear (ii) MOLECULE TYPE: Nucleic acid probe for fungal organisms (iii) HYPOTHETICAL: No (iv) ANTI-SENSE: No (xi) SEQUENCE DESCRIPTION: SEQ ID NO: 1:

GTGAAATTGT TGAAAGGGAA                                                      20

(2) INFORMATION FOR SEQ ID NO:2:

(i) SEQUENCE CHARACTERISTICS:
           (A) LENGTH: 18
           (B) TYPE: nucleic acid
           (C) STRANDEDNESS: single
           (D) TOPOLOGY: linear (ii) MOLECULE TYPE: Nucleic acid probe for fungal organisms (iii) HYPOTHETICAL: No (iv) ANTI-SENSE: No (xi) SEQUENCE DESCRIPTION: SEQ ID NO: 2:

GACTCCTTGG TCCGTGTT                                                        18

(2) INFORMATION FOR SEQ ID NO:3:

(i) SEQUENCE CHARACTERISTICS:
           (A) LENGTH: 14
           (B) TYPE: nucleic acid
           (C) STRANDEDNESS: single
           (D) TOPOLOGY: linear (ii) MOLECULE TYPE: Nucleic acid probe for Aspergillus fumigatus (iii) HYPOTHETICAL: No (iv) ANTI-SENSE: No (xi) SEQUENCE DESCRIPTION: SEQ ID NO: 3:

CTCGGAATGT ATCA                                                            14

(2) INFORMATION FOR SEQ ID NO:4:

(i) SEQUENCE CHARACTERISTICS:
           (A) LENGTH: 13
           (B) TYPE: nucleic acid
           (C) STRANDEDNESS: single
           (D) TOPOLOGY: linear (ii) MOLECULE TYPE: Nucleic acid probe for Blastomyces dermatitidis (iii) HYPOTHETICAL: No (iv) ANTI-SENSE: No (xi) SEQUENCE DESCRIPTION: SEQ ID NO: 4:

ACTCCCCCAC GGG                                                             13

(2) INFORMATION FOR SEQ ID NO:5:

(i) SEQUENCE CHARACTERISTICS:
           (A) LENGTH: 14
           (B) TYPE: nucleic acid
           (C) STRANDEDNESS: single
           (D) TOPOLOGY: linear (ii) MOLECULE TYPE: Nucleic acid probe for Candida albicans (iii) HYPOTHETICAL: No (iv) ANTI-SENSE: No (xi) SEQUENCE DESCRIPTION: SEQ ID NO: 5:

CCTCTGACGA TGCT                                                         14

(2) INFORMATION FOR SEQ ID NO:6:

(i) SEQUENCE CHARACTERISTICS:
           (A) LENGTH: 14
           (B) TYPE: nucleic acid
           (C) STRANDEDNESS: single
           (D) TOPOLOGY: linear (ii) MOLECULE TYPE: Nucleic acid probe for Coccidioides immitis (iii) HYPOTHETICAL: No (iv) ANTI-SENSE: No (xi) SEQUENCE DESCRIPTION: SEQ ID NO: 6:

TCTGGCGGTT GGTT                                                         14

(2) INFORMATION FOR SEQ ID NO:7:

(i) SEQUENCE CHARACTERISTICS:
           (A) LENGTH: 14
           (B) TYPE: nucleic acid
           (C) STRANDEDNESS: single
           (D) TOPOLOGY: linear (ii) MOLECULE TYPE: Nucleic acid probe for Cryptococcus neoformans (iii) HYPOTHETICAL: No (iv) ANTI-SENSE: No (xi) SEQUENCE DESCRIPTION: SEQ ID NO: 7:

CTCCTGTCGC ATAC                                                         14

(2) INFORMATION FOR SEQ ID NO:8:

(i) SEQUENCE CHARACTERISTICS:
           (A) LENGTH: 14
           (B) TYPE: nucleic acid
           (C) STRANDEDNESS: single
           (D) TOPOLOGY: linear (ii) MOLECULE TYPE: Nucleic acid probe for Cryptococcus neoformans (iii) HYPOTHETICAL: No (iv) ANTI-SENSE: No (xi) SEQUENCE DESCRIPTION: SEQ ID NO: 8:

AGTTCTGATC GGTG                                                         14

(2) INFORMATION FOR SEQ ID NO:9:

(i) SEQUENCE CHARACTERISTICS:
           (A) LENGTH: 14
           (B) TYPE: nucleic acid
           (C) STRANDEDNESS: single
           (D) TOPOLOGY: linear (ii) MOLECULE TYPE: Nucleic acid probe for Histoplasma capsulatum (iii) HYPOTHETICAL: No (iv) ANTI-SENSE: No (xi) SEQUENCE DESCRIPTION: SEQ ID NO: 9:

CAATCCCCCG CGGC                                                          14

(2) INFORMATION FOR SEQ ID NO:10:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Aspergillus glaucus (iii) HYPOTHETICAL: No (iv) ANTI-SENSE: No (xi) SEQUENCE DESCRIPTION: SEQ ID NO: 10:

GTGTCATGCG GCCA                                                          14

(2) INFORMATION FOR SEQ ID NO:11:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Aspergillus niger (iii) HYPOTHETICAL: No (iv) ANTI-SENSE: No (xi) SEQUENCE DESCRIPTION: SEQ ID NO: 11:

CCCTGGAATG TAGT                                                          14

(2) INFORMATION FOR SEQ ID NO:12:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Aspergillus terreus (iii) HYPOTHETICAL: No (iv) ANTI-SENSE: No (xi) SEQUENCE DESCRIPTION: SEQ ID NO: 12:

GCTTCGGCCC GGTG                                                          14

(2) INFORMATION FOR SEQ ID NO:13:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Candida glabrata (iii) HYPOTHETICAL: No (iv) ANTI-SENSE: No (xi) SEQUENCE DESCRIPTION: SEQ ID NO: 13:

```
CTTGGGACTC TCGC                                                      14

(2) INFORMATION FOR SEQ ID NO:14:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Candida guilliermondii (iii) HYPOTHETICAL: No (iv) ANTI-SENSE: No (xi) SEQUENCE DESCRIPTION: SEQ ID NO: 14:

ATATTTTGTG AGCC                                                      14

(2) INFORMATION FOR SEQ ID NO:15:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Candida kefyr (iii) HYPOTHETICAL: No (iv) ANTI-SENSE: No (xi) SEQUENCE DESCRIPTION: SEQ ID NO: 15:

TTCGGCTTTC GCTG                                                      14

(2) INFORMATION FOR SEQ ID NO:16:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Candida krusei (iii) HYPOTHETICAL: No (iv) ANTI-SENSE: No (xi) SEQUENCE DESCRIPTION: SEQ ID NO: 16:

GGGATTGCGC ACCG                                                      14

(2) INFORMATION FOR SEQ ID NO:17:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Candida lusitaniae (iii) HYPOTHETICAL: No (iv) ANTI-SENSE: No (xi) SEQUENCE DESCRIPTION: SEQ ID NO: 17:

GCCTCCATCC CTTT                                                      14
```

(2) INFORMATION FOR SEQ ID NO:18:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Candida parapsilosis (iii) HYPOTHETICAL: No (iv) ANTI-SENSE: No (xi) SEQUENCE DESCRIPTION: SEQ ID NO: 18:

ATAAGTGCAA AGAA                                              14

(2) INFORMATION FOR SEQ ID NO:19:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Candida tropicalis (iii) HYPOTHETICAL: No (iv) ANTI-SENSE: No (xi) SEQUENCE DESCRIPTION: SEQ ID NO: 19:

AGAATTGCGT TGGA                                              14

(2) INFORMATION FOR SEQ ID NO:20:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Pseudallescheria boydii (iii) HYPOTHETICAL: No (iv) ANTI-SENSE: No (xi) SEQUENCE DESCRIPTION: SEQ ID NO: 20:

GCGATGGGAA TGTG                                              14

(2) INFORMATION FOR SEQ ID NO:21:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Aspergillus flavus (iii) HYPOTHETICAL: No (iv) ANTI-SENSE: No (xi) SEQUENCE DESCRIPTION: SEQ ID NO: 21:

AGACTCGCCT CCAG                                              14

(2) INFORMATION FOR SEQ ID NO:22:

(i) SEQUENCE CHARACTERISTICS:

```
        (A) LENGTH: 14
        (B) TYPE: nucleic acid
        (C) STRANDEDNESS: single
        (D) TOPOLOGY: linear (ii) MOLECULE TYPE: Nucleic acid probe for Sporothrix schenckii (iii) HYPOTHETICAL: No (iv) ANTI-SENSE: No (xi) SEQUENCE DESCRIPTION: SEQ ID NO: 22:

CGGACCACCC GGCG                                                        14

(2) INFORMATION FOR SEQ ID NO:23:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: Nucleic acid probe for Sporothrix schenckii (iii) HYPOTHETICAL: No (iv) ANTI-SENSE: No (xi) SEQUENCE DESCRIPTION: SEQ ID NO: 23:

CGGCGGCATG CCCC                                                        14

(2) INFORMATION FOR SEQ ID NO:24:

(i) SEQUENCE CHARACTERISTICS:
        (A) LENGTH: 208
        (B) TYPE: nucleic acid
        (C) STRANDEDNESS: single
        (D) TOPOLOGY: linear (ii) MOLECULE TYPE: Acremonium species specific region of 28S gene.

(iii) HYPOTHETICAL: No (iv) ANTI-SENSE: No (xi) SEQUENCE DESCRIPTION: SEQ ID NO: 24:

GACCAGACTT GGGCTCGGTG AATCATCCGG CGTTCTCGCC GGTGCACTTT                  50

GCCGTCCCAG GCCAGCATCA GTTCGCGCCG GGGGATAAAG GTTTCGGGAA                 100

TGTAGCTCCT TCGGGAGTGT TATAGCCCGT TGCGTAATAC CCTGGCGTGG                 150

ACTGAGGTCC GCGCTCTGCA AGGATGCTGG CGTAATGGTC ATCAGTGACC                 200

CGTCTTGA                                                              208

(2) INFORMATION FOR SEQ ID NO:25:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus clavatus specific region of 28S
         gene.

(iii) HYPOTHETICAL: No (iv) ANTI-SENSE: No (xi) SEQUENCE DESCRIPTION: SEQ ID NO: 25:
```

```
GACCAGACTC GCTCGCGGGG TTCAGCCGGC ATTCGTGCCG GTGTACTTCC         50

CCGTGGGCGG GCCAGCGTCG GTTTGGGCGG CCGGTCAAAG GCCTCCGGAA        100

TGTATCACCT CTCGGGGTGT CTTATAGCCG GGGGTGCAAT GCGGCCTGCC        150

TGGACCGAGG AACGCGCTTC GGCTCGGACG CTGGCGTAAT GGTCGTAAAT        200

GACCCGTCTT GA                                                 212
```

(2) INFORMATION FOR SEQ ID NO:26:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus flavus specific region of 28S
        gene.

(iii) HYPOTHETICAL: No (iv) ANTI-SENSE: No (xi) SEQUENCE DESCRIPTION: SEQ ID NO: 26:

```
GACCAGACTC GCCTCCAGGG TTCAGCCGGC ATTCGTGCCG GTGTACTTCC         50

CTGGGGCGG GCCAGCGTCG GTTTGGGCGG CCGGTCAAAG GCTCCCGGAA         100

TGTAGTGCCC TYCGGGGCAC CTTATAGCCG GGAGTGCAAT GCGGCCAGCC        150

TGGACCGAGG AACGCGCTTC GGCACGGACG CTGGCATAAT GGTCGYAAAC        200

GACCCGTCTT GA                                                 212
```

(2) INFORMATION FOR SEQ ID NO:27:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus fumigatus specific region of 28S
        gene.

(iii) HYPOTHETICAL: No (iv) ANTI-SENSE: No (xi) SEQUENCE DESCRIPTION: SEQ ID NO: 27:

```
GACCAGACTC GCCCGCGGGG TTCAGCCGGC ATTCGTGCCG GTGTACTTCC         50

CCGTGGGCGG GCCAGCGTCG GTTTGGGCGG CCGGTCAAAG GCCCTCGGAA        100

TGTATCACCT CTCGGGGTGT CTTATAGCCG AGGGTGCAAT GCGGCCTGCC        150

TGGACCGAGG AACGCGCTTC GGCTCGGACG CTGGCGTAAT GGTCGTAAAT        200

GACCCGTCTT GA                                                 212
```

(2) INFORMATION FOR SEQ ID NO:28:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus glaucus specific region of 28S
        gene.

(iii) HYPOTHETICAL: No (iv) ANTI-SENSE: No (xi) SEQUENCE DESCRIPTION: SEQ ID NO: 28:

| | | |
|---|---|---|
| GACCAGACTC GCTTCCGGGG TTCAGCCGGC TTTCGGCCG GTGTACTTCC | | 50 |
| CCGGGGGCGG GCCAGCGTCG GTTTGGGCGG CCGGTCAAAG GCCCCTGGAA | | 100 |
| TGTAACGCCT CTCGGGCGC CTTATAGCCA GGGGTGTCAT GCGGCCAGCC | | 150 |
| TGGACCGAGG AACGCGCTTC GGCACGGACG CTGGCATAAT GGTCGTAAAC | | 200 |
| GACCCGTCTT GA | | 212 |

(2) INFORMATION FOR SEQ ID NO:29:

(i) SEQUENCE CHARACTERISTICS:
        (A) LENGTH: 213
        (B) TYPE: nucleic acid
        (C) STRANDEDNESS: single
        (D) TOPOLOGY: linear (ii) MOLECULE TYPE: Aspergillus nidulans specific region of 28S gene.

(iii) HYPOTHETICAL: No (iv) ANTI-SENSE: No (xi) SEQUENCE DESCRIPTION: SEQ ID NO: 29:

| | | |
|---|---|---|
| GACCAGACTC GGCCCCGGGG TTCARCCAGC ACTCGTGCTG GTGTACTTCC | | 50 |
| CCGGGGGCGG GCCAGCGTCG GTTTGGGCGG CCGGTCAAAG GCCCCAGGAA | | 100 |
| TGTATCGCCC TCCGGGGTTG TCTTATAGCC TGGGGTGCAA TGCGGCCAGC | | 150 |
| CCGGACCGAG GAACGCGCTT CGGCACGGAC GCTGGCGTAA TGGTCGCAAA | | 200 |
| CGACCCGTCT TGA | | 213 |

(2) INFORMATION FOR SEQ ID NO:30:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus niger specific region of 28S gene.

(iii) HYPOTHETICAL: No (iv) ANTI-SENSE: No (xi) SEQUENCE DESCRIPTION: SEQ ID NO: 30:

| | | |
|---|---|---|
| GACCAGACTC GCCCGCGGGG TTCAGCCGGC ATTCGTGCCG GTGTACTTCC | | 50 |
| CCGTGGGCGG GCCAGCGTCG GTTTGGGCGG CCGGTCAAAG GCCCCTGGAA | | 100 |
| TGTAGTRCCC TCCGGGGYAC CTTATAGCCA GGGGTGCAAT GCGGCCAGCC | | 150 |
| TGGACCGAGG AACGCGCTTC GGCACGGACG CTGGCATAAT GGTCGTAAAC | | 200 |
| GACCCGTCTT GA | | 212 |

(2) INFORMATION FOR SEQ ID NO:31:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus ochraceus specific region of 28S gene.

(iii) HYPOTHETICAL: No (iv) ANTI-SENSE: No (xi) SEQUENCE DESCRIPTION: SEQ ID NO: 31:

| | |
|---|---|
| GACCAGACTC GCCCGCGGGG TTCAGCCGGC ATTCGTGCCG GTGTACTTCC | 50 |
| CCGCGGGCGG GCCAGCGTCG GTTTGGGCGG CCGGTCAAAG GCCCCCGGAA | 100 |
| TGTAGCACCC TTCGGGGTGC CTTATAGCCG GGGGTGCAAT GCGGCCAGCC | 150 |
| TGGACCGAGG AACGCGCTTC GGCACGGACG CTGGCATAAT GGTCGTAAAC | 200 |
| GACCCGTCTT GA | 212 |

(2) INFORMATION FOR SEQ ID NO:32:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus terreus specific region of 28S gene.

(iii) HYPOTHETICAL: No (iv) ANTI-SENSE: No (xi) SEQUENCE DESCRIPTION: SEQ ID NO: 32:

| | |
|---|---|
| AACCAGACTC GCTCGCGGGG TTCAGCCGGG CTTCGGCCCG GTGTACTTCC | 50 |
| CCGCGGGCGG GCCAGCGTCG GTTTGGGCGG CCGGTCAAAG GCCTCCGGAA | 100 |
| TGTAGCGCCC TTCGGGGCGC CTTATAGCCG GGGGTGCAAT GCGGCCAGCC | 150 |
| TGGACCGAGG AACGCGCTTC GGCACGGACG CTGGCATAAT GGTTGTAAAC | 200 |
| GACCCGTCTT GA | 212 |

(2) INFORMATION FOR SEQ ID NO:33:

(i) SEQUENCE CHARACTERISTICS:
        (A) LENGTH: 213
        (B) TYPE: nucleic acid
        (C) STRANDEDNESS: single
        (D) TOPOLOGY: linear (ii) MOLECULE TYPE: Aspergillus unguis specific region of 28S gene.

(iii) HYPOTHETICAL: No (iv) ANTI-SENSE: No (xi) SEQUENCE DESCRIPTION: SEQ ID NO: 33:

| | |
|---|---|
| GACCAGACTC GGCCTCGGGG TTCAGCCAGC ACTCGTGCTG GTGTACTTCC | 50 |
| CCGGGGGCGG GCCAGCGTCG GTTTGGGCGG CCGGTCAAAG GCCCCAGGAA | 100 |
| TGTATCACCC TCCGGGGTTG TCTTATAGCC TGGGGTGCAA TGCGGCCAGC | 150 |
| CTGGACCGAG GAACGCGCTT CGGCACGGAC GCTGGCATAA TGGTTGCAAA | 200 |
| CGACCCGTCT TGA | 213 |

(2) INFORMATION FOR SEQ ID NO:34:

-continued (i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Aspergillus ustus specific region of 28S
         gene.

(iii) HYPOTHETICAL: No (iv) ANTI-SENSE: No (xi) SEQUENCE DESCRIPTION: SEQ ID NO: 34:

| | |
|---|---|
| GACCAGACTC GGCCCCGGGG TTCAGCCAGC ACTCGTGCTG GTGTACTTCC | 50 |
| CCGGGGGCGG GCCAGCGTCG GTTTGGGCGG CCGGTCAAAG GCCCCAGGAA | 100 |
| TGTGTCGCCC TCCGGGGCGT CTTATAGCCT GGGGTGCAAT GCGGCCAGCC | 150 |
| CGGACCGAGG AACGCGCTTC GGCACGGACG CTGGCGTAAT GGTCGCAAAC | 200 |
| GACCCGTCTT GA | 212 |

(2) INFORMATION FOR SEQ ID NO:35:

(i) SEQUENCE CHARACTERISTICS:
        (A) LENGTH: 208
        (B) TYPE: nucleic acid
        (C) STRANDEDNESS: single
        (D) TOPOLOGY: linear (ii) MOLECULE TYPE: Beauveria species specific region of 28S
         gene.

(iii) HYPOTHETICAL: No (iv) ANTI-SENSE: No (xi) SEQUENCE DESCRIPTION: SEQ ID NO: 35:

| | |
|---|---|
| GACCAGACTT GGGCTTGGTT GATCATCCGG GGTTCTCCCC GGTGCACTCT | 50 |
| TCCGGCCCAG GCCAGCATCA GTTCGCCCTG GGGGACAAAG GCTTCGGGAA | 100 |
| CGTGGCTCTC TCCGGGGAGT GTTATAGCCC GTTGCGTAAT ACCCTGTGGC | 150 |
| GGACTGAGGT TCGCGCATTC GCAAGGATGC TGGCGTAATG GTCATCAGTG | 200 |
| ACCCGTCT | 208 |

(2) INFORMATION FOR SEQ ID NO:36:

(i) SEQUENCE CHARACTERISTICS:
        (A) LENGTH: 213
        (B) TYPE: nucleic acid
        (C) STRANDEDNESS: single
        (D) TOPOLOGY: linear (ii) MOLECULE TYPE: Bipolaris species specific region of 28S
         gene.

(iii) HYPOTHETICAL: No (iv) ANTI-SENSE: No (xi) SEQUENCE DESCRIPTION: SEQ ID NO: 36:

| | |
|---|---|
| AGCCAGACTT GCTTGCAGTT GCTCATCCGG GCTTTTGCCC GGTGCACTCT | 50 |
| TCTGCAGGCA GGCCAGCATC AGTTTGGGCG GTGGGATAAA GGTCTCTGTC | 100 |
| ACGTACCTTC CTTCGGGTTG GCCATATAGG GGAGACGTCA TACCACCAGC | 150 |
| CTGGACTGAG GTCCGCGCAT CTGCTAGGAT GCTGGCGTAA TGGCTGTAAG | 200 |

```
CGGCCCGTCT TGA                                                     213
```

(2) INFORMATION FOR SEQ ID NO:37:

(i) SEQUENCE CHARACTERISTICS:
        (A) LENGTH: 105
        (B) TYPE: nucleic acid
        (C) STRANDEDNESS: single
        (D) TOPOLOGY: linear (ii) MOLECULE TYPE: Blastoschizomyces species specific region of 28S gene.

(iii) HYPOTHETICAL: No (iv) ANTI-SENSE: No (xi) SEQUENCE DESCRIPTION: SEQ ID NO: 37:

```
TGAAATTGTT GAAAGGGAAG GCGATGGTAG GAATAAGAGG CTGCGGTTTG              50

AAATAATTGT TTTTCGGGCC ACGGTCTCCT GAGCCTGCTT TCGCACCCGT             100

CTTGA                                                              105
```

(2) INFORMATION FOR SEQ ID NO:38:

(i) SEQUENCE CHARACTERISTICS:
        (A) LENGTH: 214
        (B) TYPE: nucleic acid
        (C) STRANDEDNESS: single
        (D) TOPOLOGY: linear (ii) MOLECULE TYPE: Blastomyces dermatitidis specific region of 28S gene.

(iii) HYPOTHETICAL: No (iv) ANTI-SENSE: No (xi) SEQUENCE DESCRIPTION: SEQ ID NO: 38:

```
GACCAGAGTC GGCCGTGGGG GTTCAGCGGG CATTCGTTGC CCGTGCACTC              50

CCCCACGGGC GGGCCAGCGT CGGTTTCGAC GGCCGGTCAA AGGCCCCCGG             100

AATGTGTCGC CTCTCGGGGC GTCTTATAGC CGGGGGTGCA ATGCGGCCAG             150

TCGGGACCGA GGAACGCGCT TCGGCACGGA CGCTGGCTTA ATGGTCGTAA             200

GCGACCCGTC TTGA                                                    214
```

(2) INFORMATION FOR SEQ ID NO:39:

(i) SEQUENCE CHARACTERISTICS:
        (A) LENGTH: 213
        (B) TYPE: nucleic acid
        (C) STRANDEDNESS: single
        (D) TOPOLOGY: linear (ii) MOLECULE TYPE: Chrysosporium species specific region of 28S gene.

(iii) HYPOTHETICAL: No (iv) ANTI-SENSE: No (xi) SEQUENCE DESCRIPTION: SEQ ID NO: 39:

```
AACCAGACTT GCGCGCGGCC GATCATCCGG TGTTCTCACC GGTGCACTCG              50

GCCGTGCTCA GGCCAGCATC GGTTTTGGCG GCTGGATAAA GGCCCTAGGA             100

ATGTGGCTCC TCTCGGGGAG TGTTATAGCC TAGGGTGCAA TGCAGCCTGC             150

TGGGACCGAG GACCGCGCTT CGGCTAGGAT GCTGGCGTAA TGGTTGTAAG             200
```

```
CGGCCCGTCT TGA                                              213

(2) INFORMATION FOR SEQ ID NO:40:

(i) SEQUENCE CHARACTERISTICS:
        (A) LENGTH: 207
        (B) TYPE: nucleic acid
        (C) STRANDEDNESS: single
        (D) TOPOLOGY: linear (ii) MOLECULE TYPE: Cladosporium species specific region of 28S
         gene.

(iii) HYPOTHETICAL: No (iv) ANTI-SENSE: No (xi) SEQUENCE DESCRIPTION: SEQ ID NO: 40:

AACCAGACTT GCTCGCGGTG TTCCGCCGGT CTTCTGACCG GTCTACTCGC        50

CGCGTTGCAG GCCAGCATCG TCTGGTGCCG CTGGATAAGA CTTGAGGAAT       100

GTAGCTCCCT CGGGAGTGTT ATAGCCTCTT GTGATGCAGC GAGCGCCGGG       150

CGAGGTCCGC GCTTCGGCTA GGATGCTGGC GTAATGGTCG TAATCCGCCC       200

GTCTTGA                                                     207

(2) INFORMATION FOR SEQ ID NO:41:

(i) SEQUENCE CHARACTERISTICS:
        (A) LENGTH: 213
        (B) TYPE: nucleic acid
        (C) STRANDEDNESS: single
        (D) TOPOLOGY: linear (ii) MOLECULE TYPE: Curvularia species specific region of 28S
         gene.

(iii) HYPOTHETICAL: No (iv) ANTI-SENSE: No (xi) SEQUENCE DESCRIPTION: SEQ ID NO: 41:

AGCCAGACTT GCTTGCAGTT GCTCATCCGG GCTTTTGCCC GGTGCACTCT        50

TCTGCAGGCA GGCCAGCATC AGTTTGGGCG GTGGGATAAA GGTCTCTGAC       100

ACGTTCCTTC CTTCGGGTTG GCCATATAGG GGAGACGTCA TACCACCAGC       150

CTGGACTGAG GTCCGCGCAT CTGCTAGGAT GCTGGCGTAA TGGCTGTAAG       200

CGGCCCGTCT TGA                                              213

(2) INFORMATION FOR SEQ ID NO:42:

(i) SEQUENCE CHARACTERISTICS:
        (A) LENGTH: 213
        (B) TYPE: nucleic acid
        (C) STRANDEDNESS: single
        (D) TOPOLOGY: linear (ii) MOLECULE TYPE: Candida albicans specific region of 28S gene.

(iii) HYPOTHETICAL: No (iv) ANTI-SENSE: No (xi) SEQUENCE DESCRIPTION: SEQ ID NO: 42:

GATCAGACTT GGTATTTTGC ATGCTGCTCT CTCGGGGGCG GCCGCTGCGG        50

TTTACCGGGC CAGCATCGGT TTGGAGCGGC AGGATAATGG CGGAGGAATG       100
```

| | |
|---|---|
| TGGCACGGCT TCTGCTGTGT GTTATAGCCT CTGACGATGC TGCCAGCCTA | 150 |
| GACCGAGGAC TGCGGTTTTT AACCTAGGAT GTTGGCATAA TGATCTTAAG | 200 |
| TCGCCCGTCT TGA | 213 |

(2) INFORMATION FOR SEQ ID NO:43:

(i) SEQUENCE CHARACTERISTICS:
        (A) LENGTH: 223
        (B) TYPE: nucleic acid
        (C) STRANDEDNESS: single
        (D) TOPOLOGY: linear (ii) MOLECULE TYPE: Candida glabrata specific region of 28S gene.

(iii) HYPOTHETICAL: No (iv) ANTI-SENSE: No (xi) SEQUENCE DESCRIPTION: SEQ ID NO: 43:

| | |
|---|---|
| GATCAGACAT GGTGTTTTGC GCCCCTTGCC TCTCGTGGGC TTGGGACTCT | 50 |
| CGCAGCTCAC TGGGCCAGCA TCGGTTTTGG CGGCCGGAAA AAACCTAGGG | 100 |
| AATGTGGCTC TGCGCCTCGG TGTAGAGTGT TATAGCCCTG GGGAATACGG | 150 |
| CCAGCCGGGA CCGAGGACTG CGATACTTGT TATCTAGGAT GCTGGCATAA | 200 |
| TGGTTATATG CCGCCCGTCT TGA | 223 |

(2) INFORMATION FOR SEQ ID NO:44:

(i) SEQUENCE CHARACTERISTICS:
        (A) LENGTH: 212
        (B) TYPE: nucleic acid
        (C) STRANDEDNESS: single
        (D) TOPOLOGY: linear (ii) MOLECULE TYPE: Candida guilliermondii specific region of 28S
        gene.

(iii) HYPOTHETICAL: No (iv) ANTI-SENSE: No (xi) SEQUENCE DESCRIPTION: SEQ ID NO: 44:

| | |
|---|---|
| GATCAGACTC GATATTTTGT GAGCCTTGCC TTCGTGGCGG GGTGACCCGC | 50 |
| AGCTTATCGG GCCAGCATCG GTTTGGGCGG TAGGATAATG GCGTAGGAAT | 100 |
| GTGACTTTRC TTCGGTGAAG TGTTATAGCC TGCGTTGATG CTGCCTGCCT | 150 |
| AGACCGAGGA CTGCGATTTT ATCAAGGATG CTGGCATAAT GATCCCAAAC | 200 |
| CGCCCGTCTT GA | 212 |

(2) INFORMATION FOR SEQ ID NO:45:

(i) SEQUENCE CHARACTERISTICS:
        (A) LENGTH: 214
        (B) TYPE: nucleic acid
        (C) STRANDEDNESS: single
        (D) TOPOLOGY: linear (ii) MOLECULE TYPE: Coccidioides immitis specific region of 28S gene.

(iii) HYPOTHETICAL: No (iv) ANTI-SENSE: No (xi) SEQUENCE DESCRIPTION: SEQ ID NO: 45:

| | |
|---|---|
| AACCAGACTC GGTCGTGGGG GCTCAGCGGG CATGAGTGCC CGTGTACTCC | 50 |
| CCCATGCTCC GGGCCAGCAT CAGTTCTGGC GGTTGGTTAA AGGCCTCTGG | 100 |
| AATGTATCGT CCTCCGGGAC GTCTTATAGC CAGGGGCGCA ATGCGGCCAG | 150 |
| CCGGGACTGA GGAACGCGCT TCGGCACGGA TGCTGGCATA ATGGTTGTAA | 200 |
| GCGGCCCGTC TTGA | 214 |

(2) INFORMATION FOR SEQ ID NO:46:

(i) SEQUENCE CHARACTERISTICS:
        (A) LENGTH: 187
        (B) TYPE: nucleic acid
        (C) STRANDEDNESS: single
        (D) TOPOLOGY: linear (ii) MOLECULE TYPE: Candida kefyr specific region of 28S gene.

(iii) HYPOTHETICAL: No (iv) ANTI-SENSE: No (xi) SEQUENCE DESCRIPTION: SEQ ID NO: 46:

| | |
|---|---|
| GATCAGACAT GGCGTTTGCT TCGGCTTTCG CTGGGCCAGC ATCAGTTTTA | 50 |
| GCGGTTGGAT AAATCCTCGG GAATGTGGCT CTGCTTCGGT AGAGTGTTAT | 100 |
| AGCCCGTGGG AATACAGCCA GCTGGGACTG AGGATTGCGA CTTTTGTCAA | 150 |
| GGATGCTGGC GTAATGGTTA AATGCCGCCC GTCTTGA | 187 |

(2) INFORMATION FOR SEQ ID NO:47:

(i) SEQUENCE CHARACTERISTICS:
        (A) LENGTH: 213
        (B) TYPE: nucleic acid
        (C) STRANDEDNESS: single
        (D) TOPOLOGY: linear (ii) MOLECULE TYPE: Candida krusei specific region of 28S gene.

(iii) HYPOTHETICAL: No (iv) ANTI-SENSE: No (xi) SEQUENCE DESCRIPTION: SEQ ID NO: 47:

| | |
|---|---|
| CGCCCGACAT GGGGATTGCG CACCGCTGCC TCTCGTGGGC GGCGCTCTGG | 50 |
| GCTTTCCCTG GGCCAGCATC GGTTCTTGCT GCAGGAGAAG GGGTTCTGGA | 100 |
| ACGTGGCTCT TCGGAGTGTT ATAGCCAGGG CCAGATGCTG CGTGCGGGGA | 150 |
| CCGAGGACTG CGGCCGTGTA GGTCACGGAT GCTGGCAGAA CGGCGCAACA | 200 |
| CCGCCCGTCT TGA | 213 |

(2) INFORMATION FOR SEQ ID NO:48:

(i) SEQUENCE CHARACTERISTICS:
        (A) LENGTH: 236
        (B) TYPE: nucleic acid
        (C) STRANDEDNESS: single
        (D) TOPOLOGY: linear (ii) MOLECULE TYPE: Cryptococcus laurentii specific region of 28S
        gene.

(iii) HYPOTHETICAL: No (iv) ANTI-SENSE: No (xi) SEQUENCE DESCRIPTION: SEQ ID NO: 48:

```
AGTCAGTCGT GTCTGGGAGG CTCAGCCGGT TCTGCCGGTG TATTCCTCTC        50

AGACGGGTCA ACATCAGTTT TGTCCGACGG ATAATGGCGG CGGGAAAGTA       100

GCACCTCCGG GTGTGTTATA GCCCGCTGTC GCATACGCCG GATGAGACTG       150

AGGCATGCAG CTCGCCTTTA TGGCAGGGGT TCGCCCACTT TCGAGCTTAG       200

GATGTTGACG TAATGGCTTT AAACGACCCG TCTTGA                      236
```

(2) INFORMATION FOR SEQ ID NO:49:

(i) SEQUENCE CHARACTERISTICS:
        (A) LENGTH: 173
        (B) TYPE: nucleic acid
        (C) STRANDEDNESS: single
        (D) TOPOLOGY: linear (ii) MOLECULE TYPE: Candida lusitaniae specific region of 28S gene.

(iii) HYPOTHETICAL: No (iv) ANTI-SENSE: No (xi) SEQUENCE DESCRIPTION: SEQ ID NO: 49:

```
AAGCAGACAC GGTTTTACCG GGCCAGCGTC GAAAAGGGGG GAGGAACAAG        50

AACTCGAGAA TGTGGCGCGC ACCTTCGGGY GCGCGTGTTA TAGCTCGTGT       100

TGACGCCTCC ATCCCTTTTC GAGGCCTGCG ATTCTAGGAC GCTGGCGTAA       150

TGGTTGCAAG CCGCCCGTCT TGA                                    173
```

(2) INFORMATION FOR SEQ ID NO:50:

(i) SEQUENCE CHARACTERISTICS:
        (A) LENGTH: 238
        (B) TYPE: nucleic acid
        (C) STRANDEDNESS: single
        (D) TOPOLOGY: linear (ii) MOLECULE TYPE: Cryptococcus neoformans var gattii
        (serotype B)specific region of 28S (iii) HYPOTHETICAL: No (iv) ANTI-SENSE: No (xi) SEQUENCE DESCRIPTION: SEQ ID NO: 50:

```
AGTCAGTCGT GTCTATTGGG TTCAGCCAGC TCTGCTGGTG TATTCCCTTT        50

AGACGGGTCA ACATCAGTTC TGATCGGTGG ATAAGGGCTG GAGGAATGTG       100

GCACTCTTCG GGGTGTGTTA TAGCCTCCTG TCGCATACAC TGGTTGGGAC       150

TGAGGAATGC AGCTCGCCTT TATGGCCGGG GTTCGCCCAC GTTCGAGCTT       200

AGGATGTTGA CAAAATGGCT TTAAACGACC CGTCTTGA                    238
```

(2) INFORMATION FOR SEQ ID NO:51:

(i) SEQUENCE CHARACTERISTICS:
        (A) LENGTH: 238
        (B) TYPE: nucleic acid
        (C) STRANDEDNESS: single
        (D) TOPOLOGY: linear (ii) MOLECULE TYPE: Cryptococcus neoformans (serotype A) specific
        region of 28S gene.

(iii) HYPOTHETICAL: No (iv) ANTI-SENSE: No (xi) SEQUENCE DESCRIPTION: SEQ ID NO: 51:

```
AGTCAGTCGT GTCTATTGGG TTCAGCCAGT TCTGCTGGTG TATTCCCTTT          50
AGACGGGTCA ACATCAGTTC TGATCGGTGG ATAAGGGCTG GGGGAATGTA         100
GCACTCTTCG GAGTGTGTTA TAGCCTCCTG TCGCATACAC TGGTTGGGAC         150
TGAGGAATGC AGCTCGCCTT TATGGCCGGG GTTCGCCCAC GTTCGAGCTT         200
AGGATGTTGA CAAAATGGCT TTAAACGACC CGTCTTGA                      238
```

(2) INFORMATION FOR SEQ ID NO:52:

(i) SEQUENCE CHARACTERISTICS:
        (A) LENGTH: 211
        (B) TYPE: nucleic acid
        (C) STRANDEDNESS: single
        (D) TOPOLOGY: linear (ii) MOLECULE TYPE: Candida parapsilosis specific region of 28S
        gene.

(iii) HYPOTHETICAL: No (iv) ANTI-SENSE: No (xi) SEQUENCE DESCRIPTION: SEQ ID NO: 52:

```
GATCAGACTT GGTATTTTGT ATGTTACTCT CTCGGGGGTG GCCTCTACAG          50
TTTACCGGGC CAGCATCAGT TTGAGCGGTA GGATAAGTGC AAAGAAATGT         100
GGCACTGCTT CGGTAGTGTG TTATAGTCTT TGTCGATACT GCCAGCTTAG         150
ACTGAGGACT GCGGCTTCGG CCTAGGATGT TGGCATAATG ATCTTAAGTC         200
GCCCGTCTTG A                                                   211
```

(2) INFORMATION FOR SEQ ID NO:53:

(i) SEQUENCE CHARACTERISTICS:
        (A) LENGTH: 238
        (B) TYPE: nucleic acid
        (C) STRANDEDNESS: single
        (D) TOPOLOGY: linear (ii) MOLECULE TYPE: Cryptococcus terreus specific region of 28S
        gene.

(iii) HYPOTHETICAL: No (iv) ANTI-SENSE: No (xi) SEQUENCE DESCRIPTION: SEQ ID NO: 53:

```
AGTCAGTCAT GTCTATTGGA CTCAGCCGGT TCTGCCGGTG TACTTCCTTT          50
AGATGGGGTC AACATCAGTT TTGATCGCTG GAAAAGGGCA GGAGGAATGT         100
AGCACTCTCG GGTGAACTTA TAGCCTTCTG TCGTATACAG TGGTTGGGAC         150
TGAGGAACGC AGCATGCCTT TATGGCCGGG GTTCGCCCAC GTACATGCTT         200
AGGATGTTGA CATAATGGCT TTAAACGACC CGTCTTGA                      238
```

(2) INFORMATION FOR SEQ ID NO:54:

(i) SEQUENCE CHARACTERISTICS:
        (A) LENGTH: 211
        (B) TYPE: nucleic acid
        (C) STRANDEDNESS: single
        (D) TOPOLOGY: linear (ii) MOLECULE TYPE: Candida tropicalis specific region of 28S gene.

(iii) HYPOTHETICAL: No (iv) ANTI-SENSE: No (xi) SEQUENCE DESCRIPTION: SEQ ID NO: 54:

| | |
|---|---|
| GATCAGACTT GGTATTTTGT ATGTTACTTC TTCGGGGTG GCCTCTACAG | 50 |
| TTTATCGGGC CAGCATCAGT TTGGGCGGTA GGAGAATTGC GTTGGAATGT | 100 |
| GGCACGGCTT CGGTTGTGTG TTATAGCCTT CGTCGATACT GCCAGCCTAG | 150 |
| ACTGAGGACT GCGGTTTATA CCTAGGATGT TGGCATAATG ATCTTAAGTC | 200 |
| GCCCGTCTTG A | 211 |

(2) INFORMATION FOR SEQ ID NO:55:

(i) SEQUENCE CHARACTERISTICS:
      (A) LENGTH: 211
      (B) TYPE: nucleic acid
      (C) STRANDEDNESS: single
      (D) TOPOLOGY: linear (ii) MOLECULE TYPE: Fusarium species specific region of 28S gene.

(iii) HYPOTHETICAL: No (iv) ANTI-SENSE: No (xi) SEQUENCE DESCRIPTION: SEQ ID NO: 55:

| | |
|---|---|
| GACCAGACTT GGGCTTGGTT AATCATCTGG GGTTCTCYCC AGTGCACTTT | 50 |
| TCCAGTCCAG GCCAGCATCA GTTTTCSCCG GGGGATAAAG RCTTCGGGAA | 100 |
| TGTGGCTCYC YYCGGGGAGT GTTATAGCCC GTTGYGTAAT ACCCTGGBGG | 150 |
| GGACTGAGGT TCGCGCWTCT GCAAGGATGC TGGCGTAATG GTCATCAACG | 200 |
| ACCCGTCTTG A | 211 |

(2) INFORMATION FOR SEQ ID NO:56:

(i) SEQUENCE CHARACTERISTICS:
      (A) LENGTH: 238
      (B) TYPE: nucleic acid
      (C) STRANDEDNESS: single
      (D) TOPOLOGY: linear (ii) MOLECULE TYPE: Filobasidium capsuligenum specific region of
      28S gene.

(iii) HYPOTHETICAL: No (iv) ANTI-SENSE: No (xi) SEQUENCE DESCRIPTION: SEQ ID NO: 56:

| | |
|---|---|
| AGTCAGTCAT GTCTATTGGA CTCAGCCGGT TCTGCCGGTG TATTTCCTTT | 50 |
| AGATGGGGTC AACATCAGTT TTGACCGTTG GATAAAGGCA GGAAGAATGT | 100 |
| AGCACTCTCG GGTGAACTTA TAGCTTCTTG TCACATACAA TGGTTGGGAC | 150 |
| TGAGGAACGC AGCATGCCTT TATGGCCGGG ATTCGTCCAC GTACATGCTT | 200 |
| AGGATGTTGA CATAATGGCT TTAAACGACC CGTCTTGA | 238 |

(2) INFORMATION FOR SEQ ID NO:57:

(i) SEQUENCE CHARACTERISTICS:
      (A) LENGTH: 238
      (B) TYPE: nucleic acid -continued (C) STRANDEDNESS: single
(D) TOPOLOGY: linear (ii) MOLECULE TYPE: Filobasidiella neoformans var bacillis pora (serotype C) specific region of 28S gene.

(iii) HYPOTHETICAL: No (iv) ANTI-SENSE: No (xi) SEQUENCE DESCRIPTION: SEQ ID NO: 57:

```
AGTCAGTCGT GTCTATTGGG TTCAGCCAGC TCTGCTGGTG TATTCCCTTT     50
AGACGGGTCA ACATCAGTTC TGATCGGTGG ATAAGGGCTG GAGGAATGTG    100
GCACTCTTCG GGGTGTGTTA TAGCCTCCTG TCGCATACAC TGGTTGGGAC    150
TGAGGAATGC AGCTCGCCTT TATGGCCGGG GTTCGCCCAC GTTCGAGCTT    200
AGGATGTTGA CAAAATGGCT TTAAACGACC CGTCTTGA                238
```

(2) INFORMATION FOR SEQ ID NO:58:

(i) SEQUENCE CHARACTERISTICS:
(A) LENGTH: 238
(B) TYPE: nucleic acid
(C) STRANDEDNESS: single
(D) TOPOLOGY: linear (ii) MOLECULE TYPE: Filobasidiella neoformans var neofor mans (serotype D) specific region of 28S gene.

(iii) HYPOTHETICAL: No (iv) ANTI-SENSE: No (xi) SEQUENCE DESCRIPTION: SEQ ID NO: 58:

```
AGTCAGTCGT GTCTATTGGG TTCAGCCAGT TCTGCTGGTG TATTCCCTTT     50
AGACGGGTCA ACATCAGTTC TGATCGGTGG ATAAGGGCTG GAGGAATGTG    100
GCACTCTTCG GGGTGTGTTA TAGCCTCCTG TCGCATACAC TGGTTGGGAC    150
TGAGGAATGC AGCTCGCCTT TATGGCCGGG GTTCGCCCAC GTTCGAGCTT    200
AGGATGTTGA CAAAATGGCT TTAAACGACC CGTCTTGA                238
```

(2) INFORMATION FOR SEQ ID NO:59:

(i) SEQUENCE CHARACTERISTICS:
(A) LENGTH: 236
(B) TYPE: nucleic acid
(C) STRANDEDNESS: single
(D) TOPOLOGY: linear (ii) MOLECULE TYPE: Filobasidium uniguttulatum specific regio n of 28S gene.

(iii) HYPOTHETICAL: No (iv) ANTI-SENSE: No (xi) SEQUENCE DESCRIPTION: SEQ ID NO: 59:

```
AGTCAGTCGT GCTCAATGGA CTCAGCCGTT CTGCGGTGTA TTTCCATTGG     50
GTGGGGTCAA CATCAGTTTT GATCGCTGGA TAAAGGCAGG AGGAATGTAG    100
CACCCCCGGG TGAACTTATA GCCTCTTGTC ACATACAGTG GTTGGGACTG    150
AGGAACGCAG CATGCCTTTA TGGCCGGGAT TCGTCCACGT ACATGCTTAG    200
GATGTTGACA TAATGGCTTT AAACGACCCG TCTTGA                   236
```

(2) INFORMATION FOR SEQ ID NO:60:

(i) SEQUENCE CHARACTERISTICS:
        (A) LENGTH: 204
        (B) TYPE: nucleic acid
        (C) STRANDEDNESS: single
        (D) TOPOLOGY: linear (ii) MOLECULE TYPE: Geotrichum species specific region of 28S g
        ene.THETICAL: No (iv) ANTI-SENSE: No (xi) SEQUENCE DESCRIPTION: SEQ ID NO: 60:

```
AATCAGACTT GGTGCTGTTG TTCAACTRTG TTTCGGCATA GTGTACTCAG         50

CAGTACTAGG CCAAGGTGGG GTGTTTGGGA GTGAAAAAGA AGTAGGAACG        100

TAACTCTTCG GAGTGTTATA GCCTACTTTC ATAGCTCCTC AGGCGCCTCA        150

GGACTGCGCT TCGGCAAGGA CCTTGGCATA ATGATTCTAT ACCGCCCGTC        200

TTGA                                                          204
```

(2) INFORMATION FOR SEQ ID NO:61:

(i) SEQUENCE CHARACTERISTICS:
        (A) LENGTH: 214
        (B) TYPE: nucleic acid
        (C) STRANDEDNESS: single
        (D) TOPOLOGY: linear (ii) MOLECULE TYPE: Histoplasma capsulatum specific region of
        28S gene.

(iii) HYPOTHETICAL: No (iv) ANTI-SENSE: No (xi) SEQUENCE DESCRIPTION: SEQ ID NO: 61:

```
GAYCAGAGTC GGCCGYGGGG GTTCAGCGGG CATTCGTTGC CCGTGCAATC     50

CCCCGCGGCC GGGCCAGCGT CGGTTTCGAC GGCCGGTCAA AGGCCCCCGG    100

AATGTGTCGC CTCTCGGGGC GTCTTATAGC CGGGGGTGCA ATGCGGCCAG    150

TCGGGACCGA GGAACGCGCT CCGGCACGGA CGCTGGCTTA ATGGTCGTCA    200

GCGACCCGTC TTGA                                           214
```

(2) INFORMATION FOR SEQ ID NO:62:

(i) SEQUENCE CHARACTERISTICS:
(A) LENGTH: 215
(B) TYPE: nucleic acid
(C) STRANDEDNESS: single
(D) TOPOLOGY: linear (ii) MOLECULE TYPE: Malbranchea species specific region of 28S g ene.THETICAL: No (iv) ANTI-SENSE: No (xi) SEQUENCE DESCRIPTION: SEQ ID NO: 62:

```
AGACAGACTC GAGCGCGGGG GCTCAGCGGG TATTGTTATG CCCGTGCACT     50

CCCCCGCGCC CGGGCCAGCA TCAGTTTTGG CGGCCGGTCA AAGGCCCTTG    100

GAATGTATCG TCCTCCGGGA CGTCTTATAG CCAAGGGTGC AATGCGGCCA    150

GCCGGGACTG AGGAACGCGC TTCGGCACGG ATGCTGGCGT AATGGCTGTA    200

AGCGGCCCGT CTTGA                                          215
```

(2) INFORMATION FOR SEQ ID NO:63:

(i) SEQUENCE CHARACTERISTICS:
        (A) LENGTH: 237
        (B) TYPE: nucleic acid
        (C) STRANDEDNESS: single
        (D) TOPOLOGY: linear (ii) MOLECULE TYPE: Mucor species specific region of 28S g
        ene.THETICAL: No (iv) ANTI-SENSE: No (xi) SEQUENCE DESCRIPTION: SEQ ID NO: 63:

```
AGCCAGACTG GTTTGACTGT AATCAACCTA GAATTCGTTC TGGGTGCACT          50

TGCAGTCTAT ACCTGCCAAC AACAGTTTGA TTTGGAGGAA AAAATTAGTA         100

GGAATGTAGC CTCTCGAGGT GTTATAGCCT ACTATCATAC TCTGGATTGG         150

ACTGAGGAAC GCAGCGAATG CCWTTAGGCR AGATTGCTGG GTGCTTTCGC         200

TAATAAATGT TAGAATTTCT GCTTCGGGTG GTGCTAA                      237
```

(2) INFORMATION FOR SEQ ID NO:64:

(i) SEQUENCE CHARACTERISTICS:
        (A) LENGTH: 209
        (B) TYPE: nucleic acid
        (C) STRANDEDNESS: single
        (D) TOPOLOGY: linear (ii) MOLECULE TYPE: Paecilomyces species specific region of 28S g
        ene.THETICAL: No (iv) ANTI-SENSE: No (xi) SEQUENCE DESCRIPTION: SEQ ID NO: 64:

```
GACCAGACTT GGGCCCGGTG GATCATCCAG CGTTCTCGCT GGTGCACTCC          50

GCCGGGTTCA GGCCAGCATC AGTTCGCCGC GGGGGAAAAA GGCTTCGGGA         100

ACGTGGCTCC TACGGGAGTG TTATAGCCCG TTGCATAATA CCCTGGGGCG         150

GACTGAGGTT CGCGCTCCGC AAGGATGCTG GCGTAATGGT CATCAGCGAC         200

CCGTCTTGA                                                     209
```

(2) INFORMATION FOR SEQ ID NO:65:

(i) SEQUENCE CHARACTERISTICS:
        (A) LENGTH: 199
        (B) TYPE: nucleic acid
        (C) STRANDEDNESS: single
        (D) TOPOLOGY: linear (ii) MOLECULE TYPE: Penicillium species specific region of 28S g
        ene.THETICAL: No (iv) ANTI-SENSE: No (xi) SEQUENCE DESCRIPTION: SEQ ID NO: 65:

```
GACCAGACTC GCCCACGGGG TTCAGCCGGC ATTCGTGCCG GTGTACTTCC          50

CCGCGGGCGG GCCAGCGTCG GTTTGGKCGG CCGGTCAAAG GCCCTCGGAA         100

TRTAACGCCC CCCGGGGCGT CTTATAGCCG AGGGTGCCAT GCGGCCAGCM         150

CAGACCGAGG AACGCGCTTC GGCTCGGACG CTGGCATAAT GGTCGTAAA         199
```

(2) INFORMATION FOR SEQ ID NO:66:

(i) SEQUENCE CHARACTERISTICS:
    (A) LENGTH: 210
    (B) TYPE: nucleic acid
    (C) STRANDEDNESS: single
    (D) TOPOLOGY: linear (ii) MOLECULE TYPE: Pseudallescheria boydii region of 28S gene.

(iii) HYPOTHETICAL: No (iv) ANTI-SENSE: No (xi) SEQUENCE DESCRIPTION: SEQ ID NO: 66:

```
GACCAGACTT GTGCCCGTCG AATCAGCCGC CGCTCGTCGG CGGCGCACTT          50

CGGCGGGCTC AGGCCAGCAT CAGTTCGCTG CAGGGGGAGA AAGGCGATGG         100

GAATGTGGCT CTTCGGAGTG TTATAGCCCG CCGCGCAATA CCCCTCGGCG         150

GACTGAGGAC CGCGCATCTG CAAGGATGCT GGCGTAATGG TCGTCAGCGA         200

CCCGTCTTGA                                                     210
```

(2) INFORMATION FOR SEQ ID NO:67:

(i) SEQUENCE CHARACTERISTICS:
    (A) LENGTH: 244
    (B) TYPE: nucleic acid
    (C) STRANDEDNESS: single
    (D) TOPOLOGY: linear (ii) MOLECULE TYPE: Rhizopus species (NO: 1) specific region of
     28S gene.

(iii) HYPOTHETICAL: No (iv) ANTI-SENSE: No (xi) SEQUENCE DESCRIPTION: SEQ ID NO: 67:

```
AGCCAGACTG GCTTGTCTGT AATCAATCTA GGTTTCGTGC CTGGATGCAC          50

TTGCAGACTA TTTGCCTGCC AACGACAATT TTTTTTGAGT GTAAAAACTA         100

TTGGAAATGT GGCCAATATT TATTTATTGG TGTTATAGTC CTTTAGAAAA         150

TACCTTGAAT TGGATTGAGG AACGCAGCGA ATGCTTCTCT TTNGAGGCAA         200

AGTCTTTTAT TGGGATTTAC GGATCAGACT GTGGCATTGT CACA               244
```

(2) INFORMATION FOR SEQ ID NO:68:

(i) SEQUENCE CHARACTERISTICS:
    (A) LENGTH: 215
    (B) TYPE: nucleic acid
    (C) STRANDEDNESS: single
    (D) TOPOLOGY: linear (ii) MOLECULE TYPE: Rhizopus species (NO: 2) specific region of 28S
         gene.

(iii) HYPOTHETICAL: No (iv) ANTI-SENSE: No (xi) SEQUENCE DESCRIPTION: SEQ ID NO: 68:

```
AGCCAGACTG GCTTGTCTGT AATCAATCTA GGCTTCGGCC TGGATGCACT          50

TGCAGGCTAT GCCTGCCAAC GACAATTTGA CTTGAGGGAA AAAACTAGGG         100

GAAATGTGGC CCACTTGTGG GTGTTATAGT CCCTTAGAAA ATACCTTGGG         150

TTGGATTGAG GAACGCAGCG AATGCTTATT GGCGAGTTTT CCAGGAAGGT         200

TTTCTGAGGT ACTAC                                               215
```

(2) INFORMATION FOR SEQ ID NO:69:

(i) SEQUENCE CHARACTERISTICS:
        (A) LENGTH: 215
        (B) TYPE: nucleic acid
        (C) STRANDEDNESS: single
        (D) TOPOLOGY: linear (ii) MOLECULE TYPE: Rhizopus species (NO: 3) specific region of 28S
        gene.

(iii) HYPOTHETICAL: No (iv) ANTI-SENSE: No (xi) SEQUENCE DESCRIPTION: SEQ ID NO: 69:

```
AGCCAGACTG GCTTGTCTGT AATCAGTCTA AGCTTCGGCT TGGATGCACT           50

TGCAGGCTAT GCCTGCCAAC GACAATTTGG CTTGAGGGAA AAAACTAAGG          100

GAAATGTGGC CCATCCGTGG GTGTTATAGT CCCTTAGAAA ATACCTTGGG          150

CTGGATTGAG GTACGCAGCG AATGCTATTT GGCGAGTTGG CTGGGAATAT          200

TTTCTGAGGT GCTTT                                                215
```

(2) INFORMATION FOR SEQ ID NO:70:

(i) SEQUENCE CHARACTERISTICS:
        (A) LENGTH: 210
        (B) TYPE: nucleic acid
        (C) STRANDEDNESS: single
        (D) TOPOLOGY: linear (ii) MOLECULE TYPE: Sporothrix species specific region of 28S gene.

(iii) HYPOTHETICAL: No (iv) ANTI-SENSE: No (xi) SEQUENCE DESCRIPTION: SEQ ID NO: 70:

```
GACCAGACTT GCGCCYCGCG GACCACCCGG CGTTCTCGCC GGTGCACTCT           50

GCGKKGCGCA GGCCAGCATC GGTTCTCCCA GGGGGACAAA GGCCGCGGGA          100

ACGTAGCTCC TTCGGGAGTG TTATAGCCCG CGGCGGCATG CCCCTGGGGG          150

GACCGAGGAC CGCGCTTCGG CAAGGATGCT GGCGTAATGG TCACCAGCGA          200

ACCGTCTTGA                                                      210
```

(2) INFORMATION FOR SEQ ID NO:71:

(i) SEQUENCE CHARACTERISTICS:
        (A) LENGTH: 208
        (B) TYPE: nucleic acid
        (C) STRANDEDNESS: single
        (D) TOPOLOGY: linear (ii) MOLECULE TYPE: Scopulariopsis brevicaulis specific region of
        28S gene.

(iii) HYPOTHETICAL: No (iv) ANTI-SENSE: No (xi) SEQUENCE DESCRIPTION: SEQ ID NO: 71:

```
GACCAGACTT GCGCCCGTCG GATCAACCGT CGCTTGCGGC GGCGCACTCC           50

GGCGGGCTCA GGCCAGCATC AGTTCGTCCG GGGGGAGAAA GGCGGCGGGA          100

ATGTGGCTCT TCGGAGTGTT ATAGCCCGCC GTGTAATACC CTCGGGTGGA          150
```

CTGAGGACCG CGCGTATGCA AGGATGCTGG CGTAATGGTC GTCAGCGACC        200

CGTCTTGA        208

(2) INFORMATION FOR SEQ ID NO:72:

(i) SEQUENCE CHARACTERISTICS:
        (A) LENGTH: 210
        (B) TYPE: nucleic acid
        (C) STRANDEDNESS: single
        (D) TOPOLOGY: linear (ii) MOLECULE TYPE: Scopulariopsis brumptii specific region of 28S
        gene.

(iii) HYPOTHETICAL: No (iv) ANTI-SENSE: No (xi) SEQUENCE DESCRIPTION: SEQ ID NO: 72:

GACCAGACTC GCGCCCGTCG GATCAGCCGT CGCTCGTCGG CGGCGCACTC        50

CGGCGGGCTC GGGCCAGCAT CAGTTCGCCT CGGGGGGAGA AAGGCGGCGG        100

GAATGTGGCT CTACGGAGTG TTATAGCCCG CCGCGTAATA CCCCCGGGCG        150

GACTGAGGAC CGCGCGTATG CAAGGATGCT GGCGTAATGG TCGTCAGCGA        200

CCCGTCTTGA        210

(2) INFORMATION FOR SEQ ID NO:73:

(i) SEQUENCE CHARACTERISTICS:
        (A) LENGTH: 214
        (B) TYPE: nucleic acid
        (C) STRANDEDNESS: single
        (D) TOPOLOGY: linear (ii) MOLECULE TYPE: Saccharomyces cerevisiae specific region of 28S
        gene.

(iii) HYPOTHETICAL: No (iv) ANTI-SENSE: No (xi) SEQUENCE DESCRIPTION: SEQ ID NO: 73:

GATCAGACAT GGTGTTTTGT GCCCTCTGCT CCTTGTGGGT AGGGGAATCT        50

CGCATTTCAC TGGGCCAGCA TCAGTTTTGG TGGCAGGATA AATCCATAGG        100

AATGTAGCTT GCCTCGGTAA GTATTATAGC CTGTGGGAAT ACTGCCAGCT        150

GGGACTGAGG ACTGCGACGT AAGTCAAGGA TGCTGGCATA ATGGTTATAT        200

GCCGCCCGTC TTGA        214

(2) INFORMATION FOR SEQ ID NO:74:

(i) SEQUENCE CHARACTERISTICS:
        (A) LENGTH: 236
        (B) TYPE: nucleic acid
        (C) STRANDEDNESS: single
        (D) TOPOLOGY: linear (ii) MOLECULE TYPE: Trichosporon beigelii specific region of
        28S gene.

(iii) HYPOTHETICAL: No (iv) ANTI-SENSE: No (xi) SEQUENCE DESCRIPTION: SEQ ID NO: 74:

```
AGTCAGTCGT GTTCTTTGGA TTCAGCCAGT TCTGCTGGTC TACTTCCTTG            50

GAACGGGTCA ACATCAGTTT TGTCCGGTGG ATAAAGGTAG TAGGAATGTG           100

ACTTCTCCGG AAGTGTTATA GCCTATTATC ACATACACTG GGTGAGACTG           150

AGGACTGCAG CTCGCCTTTA TGGCCGGCCT TCGGGCACGT TCGAGCTTAG           200

GATGTTGACA TAATGGCTTT AAACGACCCG TCTTGA                          236

(2) INFORMATION FOR SEQ ID NO: 75:

(i) SEQUENCE CHARACTERISTICS:
          (A) LENGTH: 14
          (B) TYPE: nucleic acid
          (C) STRANDEDNESS: single
          (D) TOPOLOGY: linear (ii) MOLECULE TYPE: Nucleic acid probe for Paracoccidioides
          brasiliensis (iii) HYPOTHETICAL: No (iv) ANTI-SENSE: No (xi) SEQUENCE DESCRIPTION: SEQ ID NO: 75:

ACTCCCCCGT GGTC                                                   14

(2) INFORMATION FOR SEQ ID NO: 76:

(i) SEQUENCE CHARACTERISTICS:
          (A) LENGTH: 14
          (B) TYPE: nucleic acid
          (C) STRANDEDNESS: single
          (D) TOPOLOGY: linear (ii) MOLECULE TYPE: Nucleic acid probe for Pneumocystis carinii (iii) HYPOTHETICAL: No (iv) ANTI-SENSE: No (xi) SEQUENCE DESCRIPTION: SEQ ID NO: 76:

GGAAGGGAAA TTGG                                                   14

(2) INFORMATION FOR SEQ ID NO: 77:

(i) SEQUENCE CHARACTERISTICS:
          (A) LENGTH: 223
          (B) TYPE: nucleic acid
          (C) STRANDEDNESS: single
          (D) TOPOLOGY: linear (ii) MOLECULE TYPE: Paracoccidioides brasiliensis specific region of
          28S gene.

(iii) HYPOTHETICAL: No (iv) ANTI-SENSE: No (xi) SEQUENCE DESCRIPTION: SEQ ID NO: 77:

GCGCTTGCGA CCAGAGTCGG CCGCGGGGGC TCAGCGGGCA CTCGTTGCCC            50

GTGCACTCCC CCGTGGTCGG GCCAGCGTCG GTTTCGACGG CCGGTCAAAG           100

GCCCCCGGAA TGTGTCGCCT CTCGGGGCGT CTTATAGCCG GGGGTGCAAT           150

GCGGCCAGTC GGGACCGAGG AACGCGCTCC GGCACGGACG CTGGCTTAAT           200

GGTCGTAAGC GACCCGTCTT GAA                                        223

(2) INFORMATION FOR SEQ ID NO: 78:
```

-continued

```
    (i) SEQUENCE CHARACTERISTICS:
        (A) LENGTH: 257
        (B) TYPE: nucleic acid
        (C) STRANDEDNESS: single
        (D) TOPOLOGY: linear (ii) MOLECULE TYPE: Pneumocystis carinii specific region of
         28S gene.

(iii) HYPOTHETICAL: No (iv) ANTI-SENSE: No (xi) SEQUENCE DESCRIPTION: SEQ ID NO: 78:

GCGCTTGTGA TCAGACATGC CTTTATAGGA GATGCCATTG TTTCGGCATT           50

GGCAGTATTA TCCGAATTGG CAGGCCAGCA TCGGTTTCAG TTACTGGATA          100

AAACTGGAAG AAGGTAGGCT CTCTTCGGAG GGTTTTTTAG CTTCCAGTAG          150

CTGCAGTGAC CGGGACCGGA AGGGAAATTG GGTCTTTGAA GACCTTATGA          200

TGTTGGCAGA AATGGTCCTA AGCGACCCGT CTTGAAACAC GGACCAAGGA          250

GTCTAAT                                                         257

(2) INFORMATION FOR SEQ ID NO:79:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: Nucleic Acid Primer (iii) HYPOTHETICAL: No (iv) ANTI-SENSE: No (xi) SEQUENCE DESCRIPTION: SEQ ID NO: 79:

ATCAATAAGC GGAGGAAAAG                                            20

(2) INFORMATION FOR SEQ ID NO:80:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: Nucleic Acid Primer (iii) HYPOTHETICAL: No (iv) ANTI-SENSE: No (xi) SEQUENCE DESCRIPTION: SEQ ID NO: 80:

CTCTGGCTTC ACCCTATTC                                             19
```

NUCLEIC ACID PROBES FOR THE DETECTION AND IDENTIFICATION OF FUNGI

This application is a continuation in part of Ser. No. 08/373,127 filed Jan. 13, 1995 now U.S. Pat. No. 5,763,169 and a C-I-P of Ser. No. 08/435,684 filed May 15, 1995 now U.S. Pat. No. 5,707,802.

FIELD OF INVENTION

The inventions described and claimed herein relate to the design and composition of two nucleic acid probes capable of detecting many different fungal organisms in clinical, food, environmental and other samples. The inventions described and claimed herein also relate to the design and composition of probes capable of specifically detecting and identifying Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergillus ustus,* Beauveria sp., Bipolaris sp., Blastoschizomyces sp., *Blastomyces dermatitidis, Candida albicans, Candida glabrata, Candida guilliermondii, Candida kefyr, Candida krusei, Candida lusitaniae, Candida parapsilosis, Candida tropicalis,* Chrysosporium sp., Cladosporium sp., *Coccidioides immitis, Cryptococcus neoformans* var gattii serotype B, *Cryptococcus neoformans* serotype A, *Cryptococcus laurentii, Cryptococcus terreus,* Curvularia sp., Fusarium sp., *Filobasidium capsuligenum, Filobasidiella* (Cryptococcus) *neoformans* var bacillispora serotype C, *Filobasidiella* (Cryptococcus) *neoformans* var neoformans serotype D, *Filobasidium uniguttulatum,* Geotrichum sp., *Histoplasma capsulatum,* Malbranchea sp., Mucor sp., Paecilomyces sp., *Paracoccidioides brasiliensis,* Penicillium species, *Pneumocystis carinii, Pseudallescheria boydii,* Rhizopus sp., *Sporothrix schenkii, Scopulariopsis brevicaulis* sp., *Scopulariopsis brumpti, Saccharomyces cerevisiae,* and *Trichosporon beigelii* in clinical, food, environmental and other samples.

Fungi are eukaryotic microorganisms that are universally distributed. While in nature fungi play a major role in the decomposition of plant materials, they are also responsible for spoilage of food, beverage and pharmaceutical preparations. Out of an estimated 100,000 species of fungi described by mycologists, approximately 150 species are pathogenic to man and animals. The increasing incidence of AIDS and the development of newer treatments for hematologic malignancies and organ transplants has lead to an increase in the number of immunocompromised patients. These patients have a high risk of developing fungal infections, which if not rapidly diagnosed and treated are capable of causing death in a matter of days. The number of antifungal drugs is limited and their toxic side effects on the patient are much higher than that of comparable antibacterial therapy. A rapid diagnosis of fungal infection and start of treatment is critical in these patients. Books by Kwon-Chung and Bennett, along with Sarosi and Davies, provide an overview into the medical importance of fungi.

Fungal organisms are identified by morphology and nutritional characteristics. Fungi may take anywhere from two days to several weeks to grow in culture and often the same organism can take radically different forms depending on the growth conditions. This makes timely identification difficult even for the classically trained expert and impedes the treatment of patients where rapid identification of genus and species is of medical advantage.

The incidence and distribution of major pathogenic fungi varies by geographic location. *Aspergillus fumigatus, Blastomyces dermatitidis, Candida albicans, Coccidioides immitis, Cryptococcus neoformans, Histoplasma capsulatum, Paracoccidioides brasiliensis, Pseudallescheria boydii* and *Sporothrix schenkii* represent some of the leading causes of mycotic infections.

*Aspergillus fumigatus* is among the top three causes of systemic fungal infection treated in hospitals. It usually affects patients with organ transplants, acute leukemias and burns and can be rapidly fatal if not diagnosed quickly. With over 150 species of Aspergillus present in the soil, air and water, accurate detection of *Aspergillus fumigatus* becomes extremely important. *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis* and *Aspergillus ustus* represent a majority of Aspergillus species seen in clinical specimens and their presence can cause diagnostic difficulties. *Aspergillus flavus, Aspergillus fumigatus* and *Aspergillus niger* have been linked with disease in humans, with *Aspergillus fumigatus* being the predominant pathogen in North America. A few immunologic tests exist for *Aspergillus fumigatus* but these have limited sensitivity and specificity. There are also reports of development of polymerase chain reaction based tests for *Aspergillus fumigatus* based on the amplification of the Asp fl antigen gene and a ribosomal intergenic spacer (Spreadbury et. al.). The Spreadbury technique is based on the PCR amplification of a 401 bp fragment spanning the large subunit rRNA/intergenic spacer region. This relies on a pair of primers to specifically amplify DNA from *Aspergillus fumigatus* only, and is of no utility in identifying other fungi.

*Blastomyces dermatitidis* is present in the soil, usually in bird droppings and animal feces. Infections often occur at construction sites and the ensuing lung infiltration and pneumonitis are usually fatal in immunocompromised patients. Diagnosis by culture may take weeks, and the organism is occasionally mistaken for other fungi. Existing immunological diagnostic tests are unreliable, and there is a need for rapid and reliable DNA based diagnostic tests. Similarly, *Histoplasma capsulatum* exists in the soil and is known to have infected at least 20% of the population of North America. Most infections start in the lung and resolve spontaneously, but may occasionally spread to other organs. AIDS patients represent a growing number of cases of Histoplasmosis. Diagnosis is difficult as immunological tests are often negative during the first 4–6 weeks of infection. *Coccidioides immitis* is found in abundance in the soil in Southwestern United States. Dust storms, farming, building construction, earthquakes and even hiking have been linked with outbreaks of disease. Lung infection followed by cavitation and disseminated miliary coccidioidomycosis are seen. Meningitis is usually lethal, and as with other fungi, mortality is highest in debilitated hosts. Four serotypes of *Cryptococcus neoformans* cause disease in humans. These are *Cryptococcus neoformans* serotype A, *Cryptococcus neoformans* var gatti serotype B, *Filobasidiella* (Cryptococcus) *neoformans* var bacillispora serotype C and *Filobasidiella* (Cryptococcus) *neoformans* var. neoformans serotype D. The incidence of this disease is growing rapidly, with up to 10% of HIV infected people developing cyptococcosis. DNA probes capable of detecting all 4 serotypes are required for the early diagnosis and treatment for life threatening infections like cryptococcal meningitis. A report by Stockman et. al. discusses commercial tests for Histoplasma, Blastomyces, Coccidioides, and Cryptococcus based on the 18S rRNA (Gen-Probe, Inc., San Diego, Calif.). The authors report sensitivities ranging from 87.8 to 100% and a specificity of 100%. One drawback of these probes is that these are used on rRNA extracted from fungal cultures. As some fungi may require up to 3 weeks to grow in culture, this technique cannot be used to expedite diagnosis until a culture becomes available.

Candida albicans is one of the most common causes of fungal infection in humans. It is present in the respiratory, gastrointestinal and female genital tract of healthy individuals, and acts as an opportunistic pathogen in debilitated individuals on steroid or chemotherapy. Diabetes mellitus and indwelling catheters are other predisposing causes. Immunocompromised hosts show rapid hematogenous spread of fungi. Morbidity and mortality in untreated cases is high. Candida glabrata, Candida guilliermondii, Candida kefyr, Candida krusei, Candida lusitaniae, Candida parapsilosis and Candida tropicalis are also known to cause disease in humans. DNA probes capable of identifying these individual species would eliminate the need for multiple blood cultures and lengthy biochemical speciation.

Paracoccidioidomycosis, which is a deep-seated systemic infection of humans, is a major health problem in Central and South America. The disease is caused by Paracoccidioides brasiliensis, a thermally dimorphic fungus. Classically, diagnosis has been made by detecting yeast cells with multiple buds, the distinctive "pilots wheel" morphology. Unfortunately, such forms are not always observed in clinical materials. Histologically, the yeast form of this species is sometimes difficult to distinguish from that of Histoplasma capsulatum, Blastomyces dermatitidis, Coccidioides immitis, and P. loboi. While P. brasilienis produces a glycoprotein antigen than is also diagnostic, the antigen is also produced by P. loboi. P. brasilienis can be cultured in vitro; however P. loboi cannot be cultured. P. brasiliensis is a slow growing organism that can take one to three weeks to culture for identification. Clearly, the existence of a species specific probe against P. brasiliensis would be of significant value for rapid detection and identification.

Pneumocystis carinii is a common and major opportunistic pathogenic fungus that infects immunocompromised patients. More than 80% of HIV infected patients will develop P. carinii pneumonia if not prophylactically treated to prevent infection. Therefore, this fungus is widely recognized as one of the most important causes of morbidity and mortality in AIDS patients. To date, polymerase chain reaction primers directed at six different gene targets have been developed. These include 5S and 18 rDNA genes, an intragenic transcribed spacer sequence between ribosomal genes, thymidylate synthase, dihydrofolate reductase, and large ribosomal rDNA gene of mitochondria. However, each set of primers requires a unique and specific set of PCR conditions to function optimally (Lu et al., J. Clin. Microbial. 33:2785–2788, 1995).

Recent advances in molecular techniques have led to the approach of microbe detection and identification based upon the DNA sequence of ribosomal genes. Commonly used detection techniques include either direct amplification of the ribosomal DNA (rDNA) genes by the polymerase chain reaction, or reverse transcription of the ribosomal RNA (rRNA) into complementary DNA (cDNA) followed by polymerase chain reaction amplification of the cDNA. Ribosomes are composites of unique rRNA and protein species that function in the translation of messenger RNA into protein. Evolutionary studies are consistent with the interpretation that all extant life has evolved from a single organism. Thus, all cellular organisms contain rRNA and these rRNAs are related by evolution. The evolutionary process is such that each species of organism appears to have unique regions of sequence in its ribosomal genes. The presence of these unique species specific regions allows one to design DNA probes that under conditions of hybridization will specifically bind to, and identify the polymerase chain reaction amplified DNA from only one species of fungus. For the purposes of this application, the word "primer" is used to mean a nucleotide sequence which can be extended by template-directed polymerization, and "probe" is used to mean a nucleotide sequence capable of detecting its complementary sequence by hybridization. Also, for the purpose of this application, the phrase "nucleotide sequence" is intended to include either DNA or RNA forms or modification thereof. Furthermore, those versed in the art will recognize that primer sequences can be used as probes and vice versa. The use of nucleic acid hybridization to detect specific nucleic acid sequences of interest is also described by Kohne (U.S. Pat. No. 4,851,330, 7/1989).

In prokaryotes and eukaryotes, ribosomal RNA and the corresponding rDNA genes are identified by the size of the RNA. The sizes are related in terms of sedimentation velocity or S values. Thus, for prokaryotes the values are 5S, 16S, and 23S; and for eukaryotes the values are 5S, 5.8S, 18S and 28S. Because all ribosomes perform the same function which is essential for cell viability, ribosomal sequences are largely conserved, yet certain regions of each ribosomal species are subject to more variation without consequence to function. It is these hypervariable regions that allow one to identify different species amongst members of the same genus. As noted in the references, there are several reports where 5S, 18S and the intergenic spacer between 5.8S and 28S rDNA have been used for the detection and identification of fungi (Holmes et. al., Hopfer et. al., Lott et. al., Maiwald et. al., Makimura et. al., Mitchell et. al., Nakamura et. al.). Holmes et. al. describe a PCR test based on the co-amplification of the 5S rDNA and an adjacent nontranscribed spacer region. This identifies only Candida albicans and detects other Candida species without identifying individual organisms. Hopfer et. al. and Maiwald et. al. both use universal primers to amplify 18S rDNA from several fungi including Candida sp., Aspergillus fumigatus, Cryptococcus neoformans and Trichosporon sp. These amplicons are digested with restriction enzymes and the cut fragments are sized by gel electrophoresis. This restriction fragment length polymorphism pattern enables them to identify most but not all organisms. This technique can be used on amplified DNA from a pure fungal culture. As clinical samples such as sputum usually contain multiple fungal organisms, this technique has little utility in diagnosis as multiple overlapping fragments obtained from a mix of fungi would be nearly impossible to interpret. Lott et. al. use the 5.8S RNA and the internal transcribed spacer (ITS2) to identify and speciate Candida albicans and related Candida species. Makimura amplifies a 687 bp fragment from the 18S rDNA of 25 medically important fungi and uses these in the diagnosis of Candida albicans in clinical samples. Mitchell uses nested PCR to amplify 5.8S and internal transcribed spacer (ITS) to identify Cryptococcus neoformans. No subsequent testing is done to verify the identity of the amplified DNA. Nakamura et. al. use 18S primers to detect Aspergillus fumigatus infections of the lung. Most protocols given in these references can only be used to detect an extremely limited number of fungi from a clinical specimen. Hopfer et. al. and Maiwald et. al. can identify multiple organisms from pure cultures, but their utility for clinical specimens containing multiple fungal species is limited at best.

United States patents have been issued to Weisburg et. al. for probes developed for the detection of 18S small subunit ribosomal RNA sequences in fungi. These probes will detect fungi from many species, but cannot be used easily to identify any single species. United States patents have also been issued to Milliman for probes developed for the specific detection of the bacteria *Staphylococcus aureus* based on the 16S ribosomal sequences. Hogan et. al. (European Pat. App. 0,272,009) describe one fungal probe for 18S rRNA and three fungal probes for 28S rRNA sequences. Two of these 28S probes detect several different fungi while the third probe detects *Candida krusei* from a limited panel of 10 fungi. None of the 28S probes described by Hogan et. al. is related to any of the probes described in our invention. All probes claimed in our invention can be mapped within the first 900 base pairs of a 28S gene. The probes described by Hogan et. al. are located further 3' on the 28S sequence, between base pairs 1000 and 2000 (these numbers are comparable to the primary sequence of *Saccharomyces cerevisiae* 28S rRNA gene. Genbank accession number: J01355). Leclerc et. al. have published reports analyzing the phylogenetic relationship between fungi based on partial DNA sequences of several fungal 28S genes sequenced by them. Some of the organisms claimed to have been sequenced by Leclerc are the same as some organisms sequenced by us. These are *Sporothrix schenckii, Pseudallescheria boydii, Blastomyces dermatitidis, Histoplasma capsulatum* and *Chrysosporium* sp. Leclerc et. al. have not published any sequence data in their report, and to the best of our knowledge, they have not made these sequences publicly available. The reverse-complement sequence of their sequencing primer 401 (TCCCTTTCAA CAATTTCACG) overlaps our SEQ ID NO: 1 (GTGAAATTGT TGAAAGGGAA) by 19 nucleotides and their sequencing primer 636 (GGTCCGTGTT TCAAGACGG) overlaps our SEQ ID NO: 2 (GACTCCTTGG TCCGTGTT) by 10 nucleotides. We are aware of no reports in the literature of variable regions from 28S rRNA genes of fungi being used as targets for the development of species specific diagnostic probes.

As discussed above, most present techniques for the molecular detection of fungi rely on the use of highly specific primers for the PCR amplification of only one fungal species. Those that employ "Universal" primers for a PCR amplification of DNA from multiple organisms, use post-PCR amplicon identification techniques that are useful only on pure cultures of fungi. These are not be able to identify fungi from a clinical specimen containing multiple fungal organisms. Our first aim was to develop "Universal" primers for the 28S gene. These primers would be capable of amplifying in a PCR, 28S rDNA from most fungi. Our subsequent aim was to develop species specific probes for fungi of interest, that would be used to analyze our "Universal" 28S amplicon. These species specific probes would be able to detect the presence of fungi of interest even in situations containing mixed fungal species.

One aspect of this invention is to provide nucleic acid primers capable of detecting 28S sequences from DNA or RNA of most fungi. These would be used as "Universal" primers in a polymerase chain reaction to amplify 28S sequences from any fungus present in clinical, food, environmental or other samples. These "Universal" primers would also be used to sequence the amplified DNA. The sequence obtained would be used to identify the fungus by comparing with a database of known fungal sequences.

A second aspect of this invention is to provide nucleic acid probes capable of detecting and identifying, by nucleic acid hybridization, the pathogens *Aspergillus fumigatus, Blastomyces dermatitidis, Candida albicans, Coccidioides immitis, Cryptococcus neoformans, Histoplasma capsulatum, Aspergillus flavus, Aspergillus glaucus, Aspergillus niger, Aspergillus terreus, Candida glabrata, Candida guilliermondii, Candida kefyr, Candida krusei, Candida lusitaniae, Candida parapsilosis, Candida tropicalis, Paracoccidioides brasiliensis, Pneumocystis carinii, Pseudallescheria boydii, Sporothrix schenckii* and other species by use of any of several different formats. Additionally, nucleotide sequence information is provided to identify these pathogens and other fungi by DNA sequence comparison (Table 3) or by the construction of additional probes.

SUMMARY OF THE INVENTION

Nucleic acid probes and primers are described for detecting fungi that cause disease in humans and animals, as well as spoilage of food and beverages. These probes can detect rRNA, rDNA or polymerase chain reaction products from a majority of fungi in clinical, environmental or food samples. Nucleic acid hybridization assay probes specific for *Aspergillus fumigatus, Blastomyces dermatitidis, Candida albicans, Coccidioides immitis, Cryptococcus neoformans, Histoplasma capsulatum, Aspergillus flavus, Aspergillus glaucus, Aspergillus niger, Aspergillus terreus, Candida glabrata, Candida guilliermondii, Candida kefyr, Candida krusei, Candida lusitaniae, Candida parapsilosis, Candida tropicalis, Paracoccidioides brasiliensis, Pneumocystis carinii, Pseudallescheria boydii, Sporothrix schenckii* and other species (Table 1 and Table 3) are also described.

DETAILS OF THE INVENTION

Figure 1:
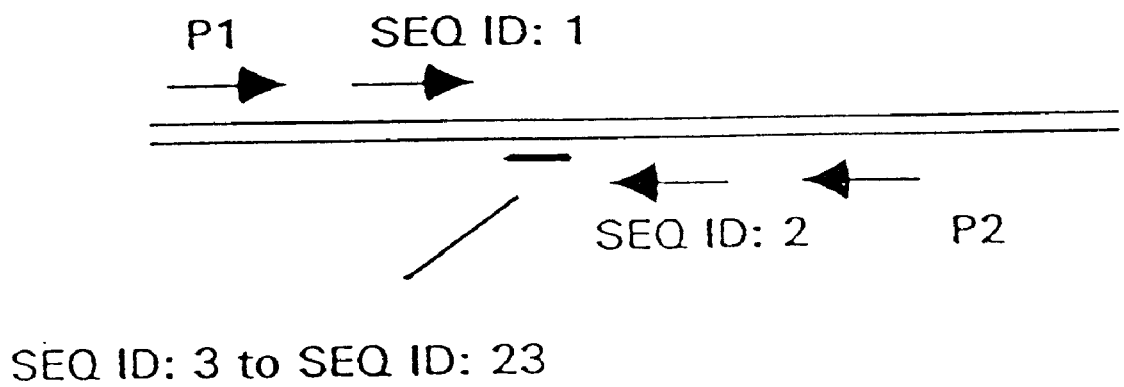
FIG. 1 represents the relative position of the sequences described on the 28S subunit of fungi.

Our first objective was to develop nucleic acid primers for use in a polymerase chain reaction to amplify 28S genes from all fungi likely to be present in a clinical sample. This amplified DNA would then be amenable to probing with several different species specific probes. Each one of these species specific probes would, under conditions of hybridization, anneal to 28S ribosomal DNA from only one species of fungus, thereby detecting and identifying the species of fungus present in the clinical sample. The 28S gene was selected as a target because it had regions that were conserved among fungi and these would provide potential annealing sites for "universal" fungal probes. The ribosomal 28S genes were also expected to have hypervariable regions that would be unique enough to provide sites for species specific probes. The large rRNA gene is called the 23S rRNA gene in prokaryotes and 28S in eukaryotes. This designation is based on the length and therefore the sedimentation coefficient of these rRNA molecules. Fungal large subunit rRNAs vary in size among different organisms and are often referred to as being 25S, 26S or 28S. Since fungi are eukaryotes, and to maintain uniformity in this application, we shall refer to fungal large subunit rRNA as 28S rRNA.

Published sequences from *Cryptococcus neoformans*, two *Candida albicans, Saccharomyces cerevisiae* and two *Schizosaccharomyces pombe* 28S genes are approximately 3.5 kilobases in length (Genbank accession numbers: L14068, L28817, X70659, J01355, Z19136 & Z19578). These four sequences were aligned, and a region of sequence variability was found clustered between coordinates 200 and 700 from the 5' end of these genes. As an initial starting point, two nucleic acid primers P1 (ATCAATAAGC GGAGGAAAAG) (SEQ ID NO: 79) and P2 (CTCTGGCTTC ACCCTATTC) (SEQ ID NO: 80) (see FIG. 1), capable of hybridizing to all 4 of the above mentioned organisms and not to human 28S sequences (GenBank accession number: M11167), were designed and used under low stringency hybridization conditions in a polymerase chain reaction to amplify approximately 800 base pairs of DNA spanning this hypervariable region from the following 34 fungi that were obtained from the Mayo Clinic fungal collection: Acremonium sp., *Aspergillus clavatus, Aspergillus fumigatus, Aspergillus glaucus, Aspergillus nidulans, Aspergillus niger, Aspergillus ochraceus, Aspergillus terreus, Aspergillus unguis, Aspergillus ustus*, Beauvaria sp., Bipolaris sp., *Blastomyces dermatitidis, Candida albicans, Candida glabrata, Candida guilliermondii, Candida kefyr, Candida krusei, Candida lusitaniae, Candida parapsilosis, Candida tropicalis*, Chrysosporium sp., Cladosporium sp., *Coccidioides immitis, Cryptococcus neoformans* serotype A, Curvularia sp., Geotrichum sp., *Histoplasma capsulatum*, Mucor sp., Penicillium sp., *Pseudallescheria boydii, Saccharomyces cerevisiae, Sporothrix schenkii* and *Trichosporon beigelii*.

DNA was extracted from the fungi listed above by the following method. A loopful of fungal culture was scraped off a culture plate using a sterile inoculation loop. The fungus was added one milliliter of sterile water in a 1.5 ml Sarsted (Newton, N.C.) screw cap microcentrifuge tube. This tube was placed in a boiling water bath for 20 minutes in order to lyse the fungus and release DNA from the cells. Two microliters of this whole cell lysate was used in a PCR to amplify 28S rDNA. All PCR amplifications were carried out as hot-start reactions in a 50 ul reaction volume using Perkin-Elmer (Norwalk, Conn.) 0.5 ml thin-wall polypropylene tubes and a Perkin-Elmer thermal cycler. Reagents added to the tube initially were 2.5 ul of 10× PCR buffer (100 mM tris pH 8.3, 500 mM KCl, 15 mM $MgCl_2$), 5.0 ul of 50% glycerol/1 mM cresol red, 8.0 ul of dNTP mix (1.25 mM each of DATP, dGTP, dTTP and dCTP), 12 picomoles of each nucleic acid primer and sterile water to make up a volume of 25 ul. A wax bead (Ampliwax Gem-100, Perkin-Elmer) was added and the tubes heated to 77° C. for 1 minute and cooled to room temperature to form a wax barrier. 2.5 ul of 10× PCR buffer, 5.0 ul of 50% glycerol/1 mM cresol red, 0.2 ul Taq polymerase (AmpliTaq 5U/ul, Perkin-Elmer) and 15.3 ul of sterile water was added to the tube along with 2.0 ul of DNA from the fungal whole cell lysate described above. 50 cycles of thermal cycling was carried out at 94° C.—30 sec, 40° C.—1 min, 72° C.—2 min. The amplified DNA was electrophoresed and purified from a low melt agarose gel by tris buffered phenol pH 8.0, phenol/chloroform/isoamyl alcohol (25:24:1 by vol.) and 3 ether extractions, followed by isopropanol precipitation and 70% ethanol wash.

We completely sequenced both strands of DNA amplified from the organisms listed above. All sequencing was carried out on an Applied Biosystems 373A sequencer. Every nucleotide in the sequences generated was verified and confirmed by examining the complementary nucleotide from the second strand sequence. We had now created a novel database consisting of nucleic acid sequences spanning a variable region of the 28S rDNA from a diverse collection of medically important fungi.

While the complete sequences for *Candida albicans, Cryptococcus neoformans* and *Saccharomyces cerevisiae* 28S genes had previously been published and deposited in GenBank, it was not obvious, nor had it been defined, whether any regions of sequence identity among these three organisms would also be conserved among all fungi of interest. DNA sequences from all the fungi in our novel 28S database had to be analyzed in order to develop "Universal" 28S probes. All sequences were subjected to extensive manipulation to identify optimal relative alignments in order to identify regions of similarity for use as "Universal" probes. The selected probe sequences had to meet several important criteria besides the condition of being present in 28S genes from most fungal species. Each probe sequence required an appropriate thermal profile, secondary structure and utility in a DNA amplification reaction. These probes were optimized to work for PCR amplification in pure cultures of fungus, as well as in the presence of DNA from multiple sources as in the case of clinical specimens. The probes were also designed to facilitate direct sequencing of the amplified DNA. Our analysis led to the discovery of the oligonucleotide probes listed in (SEQ ID NO: 1) and (SEQ ID NO: 2). (For their location, see FIG. 1.) The successful identification of these two probes ((SEQ ID NO: 1) and (SEQ ID NO: 2)) completed our first objective to develop nucleic acid probes that would hybridize to, and detect 28S rRNA and rDNA from a majority of fungi (FIG. 1 and Table 1). As shown later in this application, the novel sequence information generated by the use of our "Universal" probes allowed us to develop species-specific probes ((SEQ ID NO: 3) to (SEQ ID NO: 23), (SEQ ID NO: 75) and (SEQ ID NO: 76)) capable of identifying 21 different disease-causing fungi.

TABLE 1

Presence of hybridization sites for probes SEQ ID NO: 1 and SEQ ID NO: 2 in 28S nucleic acid sequences

|  | SEQ ID NO: 1 | SEQ ID NO: 2 |
|---|---|---|
| Acremonium sp. | + | + |
| *Aspergillus clavatus* | + | + |
| *Aspergillus flavus* | + | + |
| *Aspergillus fumigatus* | + | + |
| *Aspergillus glaucus* | + | + |
| *Aspergillus nidulans* | + | + |
| *Aspergillus niger* | + | + |
| *Aspergillus ochraceus* | + | + |
| *Aspergillus terreus* | + | + |
| *Aspergillus unguis* | + | + |
| *Aspergillus ustus* | + | + |
| Beauvaria sp. | + | + |
| Bipolaris sp. | + | + |
| *Blastomyces dermatitidis* | + | + |
| Blastoschizomyces sp. | + | + |
| *Candida albicans* | + | + |
| *Candida glabrata* | + | + |
| *Candida guilliermondii* | + | + |
| *Candida kefyr* | + | + |
| *Candida krusei* | + | + |
| *Candida lusitaniae* | + | + |
| *Candida parapsilosis* | + | + |
| *Candida tropicalis* | + | + |
| Chrysosporium sp. | + | + |
| Cladosporium sp. | + | + |
| *Coccidioides immitis* | + | + |
| *Cryptococcus laurentii* | + | + |
| *Cryptococcus neoformans* serotype A | + | + |
| *Cryptococcus neoformans* var. *gattii* serotype B | + | + |
| *Cryptococcus terreus* | + | + |
| Curvularia sp. | + | + |
| *Filobasidiella (Cryptococcus) neoformans* var *bacillispora* serotype C | + | + |

TABLE 1-continued

Presence of hybridization sites for probes SEQ ID NO: 1 and SEQ ID NO: 2 in 28S nucleic acid sequences

| | SEQ ID NO: 1 | SEQ ID NO: 2 |
|---|---|---|
| *Filobasidiella* (*Cryptococcus*) *neoformans* var *neoformans* serotype D | + | + |
| *Filobasidium capsuligenum* | + | + |
| *Filobasidium uniguttulatum* | + | + |
| Fusarium sp. | + | + |
| Geotrichum sp. | + | + |
| *Histoplasma capsulatum* | + | + |
| Malbranchea sp. | + | + |
| Mucor sp. | + | + |
| Paecilomyces sp. | + | + |
| Penicillium sp. | + | + |
| *Pseudallescheria boydii* | + | + |
| Rhizopus sp. | + | + |
| *Saccharomyces cerevisiae* | + | + |
| *Scopulariopsis brevicaulis* | + | + |
| *Scopulariopsis brumptii* | + | + |
| *Sporothrix schenckii* | + | + |
| *Trichosporon beigelii* | + | + |
| *Paracoccidioides brasiliensis* | + | + |
| *Pneumocystis carinii* | + | + |
| Human | − | + |

Probes SEQ ID NO: 1 and SEQ ID NO: 2 were used to successfully amplify (Table 2) and sequence DNA (Table 3) spanning this variable region from the following 51 organisms: Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergillus ustus,* Beauvaria sp., Bipolaris sp., *Blastomyces dermatitidis,* Blastoschizomyces sp., *Candida albicans, Candida glabrata, Candida guilliermondii, Candida kefyr, Candida krusei, Candida lusitaniae, Candida parapsilosis, Candida tropicalis,* Chrysosporium sp., Cladosporium sp., *Coccidioides immitis, Cryptococcus neoformans* serotype A, *Cryptococcus neoformans* var. gattii serotype B, *Cryptococcus terreus, Cryptococcus laurentii,* Curvularia sp., *Filobasidiella* (Cryptococcus) *neoformans* var bacillispora serotype C, *Filobasidiella* (Cryptococcus) *neoformans* var neoformans serotype D, *Filobasidium capsuligenum, Filobasidium uniguttulatum,* Fusarium sp., Geotrichum sp., *Histoplasma capsulatum,* Maibranchea sp., Mucor sp., Paecilomyces sp., Penicillium sp., *Pseudallescheria boydii,* Rhizopus sp., *Saccharomyces cerevisiae, Scopulariopsis brevicaulis, Scopulariopsis brumptii, Sporothrix schenkii, Paracoccidioides brasiliensis, Pneumocystis carinii,* and *Trichosporon beigelii.* This list contains all 4 serotypes (A, B, C and D) of *Cryptococcus neoformans.* This sequence information generated by the use of probes SEQ ID NO: 1 and SEQ ID NO: 2 expanded the size of our database consisting of fungal 28S sequences. All amplified DNA was sequenced across both strands from a minimum of two different isolates of each organism to ensure accuracy of the data generated.

TABLE 2

Polymerase chain reaction amplification of 28S rDNA with probes SEQ ID NO: 1 and SEQ ID NO: 2.

| | PCR with SEQ ID NO: 1 & NO: 2 |
|---|---|
| Acremonium sp. | + |
| *Aspergillus clavatus* | + |
| *Aspergillus flavus* | + |
| *Aspergillus fumigatus* | + |
| *Aspergillus glaucus* | + |
| *Aspergillus nidulans* | + |
| *Aspergillus niger* | + |
| *Aspergillus ochraceus* | + |
| *Aspergillus terreus* | + |
| *Aspergillus unguis* | + |
| *Aspergillus ustus* | + |
| Beauvaria sp. | + |
| Bipolaris sp. | + |
| *Blastomyces dermatitidis* | + |
| Blastoschizomyces sp. | + |
| *Candida albicans* | + |
| *Candida glabrata* | + |
| *Candida guilliermondii* | + |
| *Candida kefyr* | + |
| *Candida krusei* | + |
| *Candida lusitaniae* | + |
| *Candida parapsilosis* | + |
| *Candida tropicalis* | + |
| Chrysosporium sp. | + |
| Cladosporium sp. | + |
| *Coccidioides immitis* | + |
| *Cryptococcus laurentii* | + |
| *Cryptococcus neoformans* serotype A | + |
| *Cryptococcus neoformans* var. gattii serotype B | + |
| *Cryptococcus terreus* | + |
| Curvularia sp. | + |
| *Filobasidiella* (*Cryptococcus*) *neoformans* var *bacillispora* serotype C | + |
| *Filobasidiella* (*Cryptococcus*) *neoformans* var *neoformans* serotype D | + |
| *Filobasidium capsuligenum* | + |
| *Filobasidium uniguttulatum* | + |
| Fusarium sp. | + |
| Geotrichum sp. | + |
| *Histoplasma capsulatum* | + |
| Malbranchea sp. | + |
| Mucor sp. | + |
| Paecilomyces sp. | + |
| Penicillium sp. | + |
| *Pseudallescheria boydii* | + |
| Rhizopus sp. | + |
| *Saccharomyces cerevisiae* | + |
| *Scopulariopsis brevicaulis* | + |
| *Scopulariopsis brumptii* | + |
| *Sporothrix schenckii* | + |
| *Trichosporon beigelii* | + |
| *Paracoccidioides brasiliensis* | + |
| *Pneumocystis carinii* | + |
| Human | − |

This list of fungi sequenced by us represents organisms responsible for most cases of subcutaneous and deep mycotic infections in humans and also includes saprophytes (non-pathogenic fungi) commonly encountered in clinical isolates. Since the two probes (SEQ ID NO: 1 and SEQ ID NO: 2) hybridize to 28S rDNA from all the fungi listed above, they are capable of diagnosing the presence of a majority of fungi that are likely to be present in a clinical specimen. They are believed to be primers for universally detecting fungi.

Probes listed in SEQ ID NO: 1 and SEQ ID NO: 2 were also checked for their potential ability to hybridize to, and amplify (in a polymerase chain reaction) 23S sequences from bacteria by searching for hybridization sites among the 539 bacterial 23S genes listed in GenBank. Bacterial 23S rDNAs do not have suitable hybridization sites for SEQ ID NO: 1 and SEQ ID NO: 2 and these two probes should not be able to amplify bacterial DNA under stringent conditions.

Our second objective was to develop species specific probes, which under hybridization conditions, would detect *Aspergillus fumigatus, Blastomyces dermatitidis, Candida albicans, Coccidioides immitis, Cryptococcus neoformans, Histoplasma capsulatum, Aspergillus flavus, Aspergillus glaucus, Aspergillus niger, Aspergillus terreus, Candida glabrata, Candida guilliermondii, Candida kefyr, Candida krusei, Candida lusitaniae, Candida parapsilosis, Candida tropicalis, Paracoccidioides brasiliensis, Pneumocystis carinii, Pseudallescheria boydii,* and *Sporothrix schenckii.* We used our database of fungal 28S nucleic acid sequences to create a multiple sequence alignment of all the organisms that we had sequenced. Every individual sequence was subjected to intensive comparison with all other sequences in our database in order to discover unique regions of sequence that would be present only in the fungus of interest, and would be absent in all other fungi. When unique stretches of sequence were identified, these were further analyzed for thermal profile and secondary structure. Each probe constructed by us will, under conditions of hybridization, specifically hybridize to and detect, nucleic acid sequence from the unique region of only one specific target fungus. Those versed in the art will recognize that specification of a single-stranded DNA sequence implies the utility of the complementary DNA sequence, as well as the two equivalent RNA sequences. Furthermore, sequences incorporating modification of any of the moieties comprising the nucleic acid (i.e., the base, the sugar or the backbone) are functional equivalents of the sequence. It should also be recognized that these additional sequences can potentially serve as probes or primers. Finally, those versed in the art recognize that comparisons of extensive DNA sequences provides enough variability and uniqueness to speciate organisms (Table 3).

The nucleic acid sequences for these species specific synthetic probes are listed in SEQ ID NO: 3 to SEQ ID NO: 23, SEQ ID NO: 75 and SEQ ID NO: 76. There are two probes specific for *Cryptococcus neoformans,* two probes specific for *Sporothrix schenckii,* and one probe each for *Aspergillus fumigatus, Blastomyces dermatitidis, Candida albicans, Coccidioides immitis, Histoplasma capsulatum, Aspergillus flavus, Aspergillus glaucus, Aspergillus niger, Aspergillus terreus, Candida glabrata, Candida guilliermondii, Candida kefyr, Candida krusei, Candida lusitaniae, Candida parapsilosis, Candida tropicalis, Paracoccidioides brasiliensis, Pneumocystis carinii,* and *Pseudallescheria boydii* 28S rRNA and rDNA. (See Tables 4–8 and further discussion below.)

All species specific probes developed by us are novel and to the best of our knowledge have not been reported in the literature. While all 28S genes sequenced by us had several regions that were different among the various species analyzed, the regions that would function best as species specific probes under conditions of hybridization were not obvious. Extensive analysis of each 28S sequence yielded several potential probe sites. These were studied in detail to enable the selection of optimal unique sites for each probe, based on the need to obtain optimal hybridization characteristics under the test conditions. The highly specific hybridization characteristics of all probe sequences developed by us were then validated by experimental results. The prior existence in GenBank of sequences for *Candida albicans* and serotypes A and B (GenBank accession numbers L14067 and L14068) of *Cryptococcus neoformans* 28S genes was in itself not sufficient to enable even an individual versed in this field to develop specific probes for either of these two organisms. We had to obtain novel 28S sequence from *Candida albicans, Candida glabrata, Candida guilliermondii, Candida kefyr, Candida krusei, Candida lusitaniae, Candida parapsilosis, Candida tropicalis, Cryptococcus neoformans* serotype A, *Cryptococcus neoformans* var. gattii serotype B, *Cryptococcus terreus, Cryptococcus laurentii, Filobasidiella* (Cryptococcus) *neoformans* var bacillispora serotype C, *Filobasidiella* (Cryptococcus) *neoformans* var neoformans serotype D, *Filobasidium capsuligenum* and *Filobasidium uniguttulatum* before we were able to identify potential regions for the development of species specific probes for these two fungal organisms that would not cross react with the others listed above.

Our modification of the Chomczynski technique (see Example 2, below) allows us to obtain DNA from any clinical specimen, irrespective of source (see Table 10 for a variety of clinical specimens tested), within a 3 hour period. The PCR amplification and subsequent probing can be accomplished with ease within a 24 hour period. The final identification is therefore possible in a day as opposed to several days or weeks required by traditional methods. This speed and sensitivity of diagnosis can make a difference between life and death in debilitated patients battling fungal diseases of undetermined cause. Rapid diagnosis will allow physicians to immediately direct their therapy towards curing the identified causative fungus, rather than wait for days or weeks while the patient succumbs to an unknown fungus.

Our probes have the ability to pick out the correct target organism even in a mixed fungal infection because of their high level of specificity. The methods of Hopfer et. al. and Maiwald et. al., do not allow identification of individual species in a mixed fungal infection because restriction fragment length polymorphism results are nearly impossible to interpret when multiple organisms contribute to the restriction fragments. Their method can therefore only be used on a pure culture, and this also does not save any diagnostic time, because the fungus first has to be grown in culture.

The probes developed by us allow rapid species identification of a large number of pathogenic fungi by using multiple probes against only one PCR amplified fragment of DNA. Coupled with our modified DNA extraction technique and our ability to accurately diagnose in the case of mixed organisms, this strategy can provide the greatest amount of diagnostic information in the shortest amount of time. This diagnostic strategy is also amenable to automation, which can result in even greater savings in time, money and effort.

The sequences and the complement of the sequences claimed in this disclosure, along with any modifications to these sequences, may potentially be utilized in assays for the identification of fungi based on several existing methodologies, as well as future improvements and alterations of this technology. These techniques include, but are not limited to, assays based on hybridization, ligation, polymerization, depolymerization, sequencing, chemical degradation, enzymatic digestion, electrophoresis, chromatography and amplification. Furthermore, all such variations ultimately are based in some selection or amplification process, some ligand or some nucleic acid moiety that recognizes or utilizes the sequences (SEQ ID NO: 1) to (SEQ ID NO: 23), (SEQ ID NO: 75) and (SEQ ID NO: 76) claimed in this application. Such variations include but are not limited to use of a variety of linear or exponential target amplification schemes, such as, any of the myriad forms of PCR, the ligase chain reaction, Q-beta repliase, etc.; direct detection of species-specific nucleic acid purified or extracted from pure fungal culture using a probe selected from the group (SEQ ID NO: 3) to (SEQ ID NO: 23), (SEQ ID NO: 75) and (SEQ ID NO: 76); use of the complementary DNA forms of (SEQ ID NO: 1) to (SEQ ID NO: 23), (SEQ ID NO: 75) and (SEQ ID NO: 76); use of the RNA forms of these sequences and their complements; and use of derivatives of these DNA or RNA sequences by the addition of one or more reporter moieties from a variety of labels including nucleic acid sequences, proteins, signal generating ligands such as acridinium esters, and/or paramagnetic particles. These techniques may be utilized with DNA, RNA or modified derivatives used as either the target or the detection molecule.

In addition to the 25 sequences SEQ ID NO: 1 to SEQ ID NO: 23, SEQ ID NO: 75 and SEQ ID NO: 76, we also describe an additional 53 sequences SEQ ID NO: 24 to SEQ ID NO: 74, SEQ ID NO: 77 and SEQ ID NO: 78. These 53 sequences are inclusive of SEQ ID NO: 3 to SEQ ID NO: 23, SEQ ID NO: 75 and SEQ ID NO: 76 and are shown as a multiple sequence alignment (Table 3) with coordinate 1 corresponding to base #431 of a reference *S. cerevisiae* 28S rRNA gene. (The numbers are comparable to the primary sequence of *S. cerevisiae* 28S rRNA gene. Genbank accession number: J01355). These sequences were obtained by amplifying and sequencing 28S rDNA from various fungi with primers SEQ ID NO: 1 and SEQ ID NO: 2. (SEQ ID NO: 1 corresponds to coordinates 403–422 and the SEQ ID NO: 2 corresponds to coordinates 645–662 of the reference *S. cerevisiae* gene).

An analysis of these aligned sequences enabled us to develop the species specific probes SEQ ID NO: 3 to SEQ ID NO: 23, SEQ ID NO: 75 and SEQ ID NO: 76 and sites for these probes are shown underlined. These 53 aligned sequences contain sufficient variability, to enable a person versed in this art, to develop additional species specific hybridization probes in the 10–50 nucleotide length. Similarly, longer species specific hybridization probes encompassing the entire 200+ nucleotide length can also be envisioned. Species identification may also be accomplished by direct DNA sequence determination of any DNA amplified with primers SEQ ID NO: 1 and SEQ ID NO: 2. If the derived sequence matches approximately 98% or more of any sequence in SEQ ID NO: 24 to SEQ ID NO: 74, SEQ ID NO: 77 and SEQ ID NO: 78, then the identity of the organism can be ascertained. Additionally, we recognize that parts of SEQ ID NO: 24 to SEQ ID NO: 74, SEQ ID NO: 77 and SEQ ID NO: 78 may be specific for groups of fungi arranged phylogenetically at the level of genus or higher. SEQ ID NO: 24 to SEQ ID NO: 74, SEQ ID NO: 77 and SEQ ID NO: 78, their complements, along with any modification to these sequences may also potentially be utilized in assays for the identification of fungi based on existing methodologies and future technologies as noted above for SEQ ID NO: 1 to SEQ ID NO: 23, SEQ ID NO: 75 and SEQ ID NO: 76.

TABLE 3

Multiple Sequence alignment for (SEQ ID NO: 24) through
(SEQ ID NO: 74), (SEQ ID NO: 77) AND (SEQ ID NO: 78)

```
                1                                                                          70
{Rhizo2} AGCCAGACTG GCTTGTCTGT AATCAATCTA GGCTTCG.GC CTGGATGCAC TTGCAGGCTA ..TGCCTGCC
{Rhizo3} AGCCAGACTG GCTTGTCTGT AATCAGTCTA AGCTTCG.GC TTGGATGCAC TTGCAGGCTA ..TGCCTGCC
{Rhizo1} AGCCAGACTG GCTTGTCTGT AATCAATCTA GGTTTCGTGC CTGGATGCAC TTGCAGACTA TTTGCCTGCC
{Mucor_} AGPCAGACTG GTTTGACTGT AATCAAPCTA GAATTCGTTC .TGGGTGCAC TTGCAGTCTA ..TACCTGCC
{C_Terr} AGTCAGTCAT GTCTATTGGA CTCAGPPGGT TCT......G CCGGTGTACT TCCTTTAGAT GGGGTCAAC.
{F_Caps} AGTCAGTCAT GTCTATTGGA CTCAGCCGGT TCT......G CCGGTGTATT TCCTTTAGAT GGGGTCAAC.
{F_Unig} AGTCAGTCGT GCTCAATGGA CTCAGCCG.. TTC......T GCGGTGTATT TCCATTGGGT GGGGTCAAC.
{C_Neob} AGTCAGTCGT GTCTATTGGG TTCAGCCAGC TCT......G CTGGTGTATT CCCTTTAGA. CGGGTCAAC.
{F_Neoc} AGTCAGTCGT GTCTATTGGG TTCAGCCAGC TCT......G CTGGTGTATT CCCTTTAGA. CGGGTCAAC.
{F_Neod} AGTCAGTPGT GTCTATTGGG TTCAGPCAGT TCT......G CTGGTGTATT CCCTTTAGA. CGGGTCAAC.
{C_Neog} AGTCAGTCGT GTCTATTGGG TTCAGPCAGT TCT......G CTGGTGTATT PPCTTTAGA. CGGGTCAAC.
{T_Beig} AGTCAGTCGT GTTCTTTGGA TTCAGCCAGT TCT......G CTGGTCTACT TCCTTGGAA. CGGGTCAAC.
{C_Laur} AGTCAGTCGT GTCTGGGAGG CTCAGCCGGT TCT......G CCGGTGTATT CCTCTCAGA. CGGGTCAAC.
{Beauve} GAPCAGACTT GGGCTTGGTT GATCATPPGG GGTTC.TCC. CCGGTGCACT CTTCC.GGCC CAGGCCAGC.
{Fusari} GACCAGACTT GGGCTTGGTT AATCATCTGG GGTTC.TCY. CCAGTGCACT TTTCC.AGTC CAGGCCAGC.
{Acremo} GACCAGACTT GGGCTCGGTG AATCATCCGG CGTTC.TCG. CCGGTGCACT TTGCC.GTCC CAGGCCAGC.
{Paecil} GACCAGACTT GGGCCCGGTG GATCATCCAG CGTTC.TCG. CTGGTGCACT CCGCCGGGTT CAGGCCAGC.
{P_Boyd} GACCAGACTT GTGCCCGTCG AATCAGCCGC CGCTCGTCG. GCGGCGCACT TCGGCGGGCT CAGGCCAGC.
{S_Brum} GACCAGACTC GCGCCCGTCG GATCAGCCGT CGCTCGTCG. GCGGCGCACT CCGGCGGGCT CGGGCCAGC.
{S_Brev} GACCAGACTT GCGCCCGTCG GATCAACCGT CGCTTG.OG. GCGGCGCACT CCGGCGGGCT CAGGCCAGC.
{Sporot} GACCAGACTT GCGCCYCGCG GACCACCCGG CGTTC.TCG. CCGGTGCACT CTGCGKKGCG CAGGCCAGC.
{B_Derm} GACCAGAGTC GGCCGTGGGG GTTCAGCGGG CATTCGT.TG CCCGTGCACT CCCCCACGGG CGGGCCAGC.
{H_Caps} GAYCAGAGTC GGCCGYGGGG GTTCAGCGGG CATTCGT.TG CCCGTGCAAT CCCCCGCGGC CGGGCCAGC.
{A_Nidu} GACCAGACTC GGCCCC.GGG GTTCAGCCAG CACTCG..TG CTGGTGTACT TCCCCGGGGG CGGGCCAGC.
{A_Ungu} GACCAGACTC GGCCTC.GGG GTTCAGCCAG CACTCG..TG CTGGTGTACT TCCCCGGGGG CGGGCCAGC.
{A_Ustu} GACCAGACTC GGCCCC.GGG GTTCAGCCAG CACTCG..TG CTGGTGTACT TCCCCGGGGG CGGGCCAGC.
{A_Clav} GACCAGACTC GCTCGC.GGG GTTCAGCCGG CATTCG..TG CCGGTGTACT TCCCCGTGGG CGGGCCAGC.
{A_Fumi} GACCAGACTC GCCCGC.GGG GTTCAGCCGG CATTCG..TG CCGGTGTACT TCCCCGTGGG CGGGCCAGC.
{A_Flav} GACCAGACTC GCCTCC.AGG GTTCAGCCGG CATTCG..TG CCGGTGTACT TCCCTGGGGG CGGGCCAGC.
{A_Ochr} GACCAGACTC GCCCGC.GGG GTTCAGCCGG CATTCG..TG CCGGTGTACT TCCCCGCGGG CGGGCCAGC.
{A_Nige} GACCAGACTC GCCCGC.GGG GTTCAGCCGG CATTCG..TG CCGGTGTACT TCCCCGTGGG CGGGCCAGC.
{A_Terr} AACCAGACTC GCTCGC.GGG GTTCAGCCGG GCTTCG..GC CCGGTGTACT TCCCCGCGGG CGGGCCAGC.
{A_Glau} GACCAGACTC GCTTCC.GGG GTTCAGCCGG CTTTCG..GG CCGGTGTACT TCCCCGGGGG CGGGCCAGC.
{Penici} GACCAGACTC GCCCAC.GGG GTTCAGCCGG CATTCG..TG CCGGTGTACT TCCCCGCGGG CGGGCCAGC.
{C_Immi} AACCAGACTC GGTCGTGGGG GCTCAGCGGG CATGAGT.GC CCGTGTACTC CCCCATGCTC CGGGCCAGC.
{Bipola} AGCCAGACTT GCTTGCAGTT GCTCATCCGG GCTTT.T.GC CCGGTGCACT CTTCTGCAGG CAGGCCAGC.
```

TABLE 3-continued

Multiple Sequence alignment for (SEQ ID NO: 24) through
(SEQ ID NO: 74), (SEQ ID NO: 77) AND (SEQ ID NO: 78)

```
{Curvul} AGCCAGACTT GCTTGCAGTT GCTCATCCGG GCTTT.T.GC CCGGTGCACT CTTCTGCAGG CAGGCCAGC.
{Chryso} AACCAGACTT GCGCGCGGCC GATCATCCGG TGTTC.T.CA CCGGTGCACT CGGCCGTGCT CAGGICAGC.
{Clados} AACCAGACTT GCTCGCGGT. GTTCCGCCGG TCTTC.T.GA CCGGTCTACT CGCCGCGTTG CAGGCCAGC.
{Malbra} AGACAGACTC GAGCGCGGGA GCTCAGCGGG TATTGTTATG CCCGTGCACT CCCCCGCGCC CAGGCCAGC.
{C_Para} GATCAGACTT GGTATTTTGT ATG..TTACT CTCTCGGGG. ..GTGGCCTC TACAGTTTAC CGGGCCAGC.
{C_Trop} GATCAGACTT GGTATTTTGT ATG..TTACT TCTTCGGGG. ..GTGGCCTC TACAGTTTAT CGGGCCAGC.
{C_Albi} GATCAGACTT GGTATTTTGC ATG..CTGCT CTCTCGGGG. ..GCGGCCGC TGCGGTTTAC CGGGCCAGC.
{C_Quil} GATCAGACTC GATATTTTGT GAGCCTTGCC TTCGTGGCG. ..GGGTGACC GCAGCTTAT CGGGCCAGC.
{C_Glab} GATCAGACAT GGTGTTTTGC GCCCCTTGCC TCTCGTGGGC TTGGGACTCT CGCAGCTCAC TGGGCCAGC.
{S_Cere} GATCAGACAT GGTGTTTTGT GCCCTCTGCT CCTTGTGGGT AGGGCAATCT CGCATTTCAC TGGGCCAGC.
{C_Kefy} GATCAGACAT GGCGTTTGCT .......... .......... .........T CGGCTTTCGC TGGGCCAGC.
{Geotri} AATCAGACTT GGTGCTGT.. .TGTTCAACT RTGTTTCGGC ATAGTGTACT CAGCAGTACT AGGCCAAGG.
{C_Lusi} AAGCAGACAC GGT....... .......... .......... .......... .....TTTAC CGGGCCAGC.
{C_Krus} CGCCCGACAT GGGGATTGCG CACCGCTGCC TCTCGTGGGC ..GGCGCTCT GGGCTTTCCC TGGGCCAGC.
{Blasch} .......... .......... .......... .......... .......... .......... ..........
{P_Braz} ACCAGAGTCG GCCGCGGGGG CTCAGCGGGC ACTCGT.TGC CCGTGCACTC CCCCGTC... .GTCGGGCCA
{Pc_Hum} ATCAGACATG CCTTTATAGG AGATGCCATT GTT..TCGGC ATTGGCAGTA TTATCCGAAT TGGCAGGCCA
         71                                                                      140
{Rhizo2} AACGACAATT TGACTTGAGG GAAAAAACTA GGGGAAATGT GGCC...... CACTTGTGGG TGTTATAGTC
{Rhizo3} AACGACAATT TGGCTTGAGG GAAAAAACTA AGGGAAATGT GGCC...... CATCCGTGGG TGTTATAGTC
{Rhizo1} AACGACAATT TTTTTTGAGT GTAAAAACTA TTGGAAATGT GGCCAATATT TATTTATTGG TGTTATAGTC
{Mucor_} AACAACAGTT TGATTTGGAG GAAAAAATTA GTAGGAATGT AGCC...... ....TCTCGA GGTGTTATAG
{C_Terr} .ATCAGTTTT .GATCGCTGG AAAAGGGCAG GAGGAATGTA GCACTC.TCG GGTGAACTTA TAGCCTTCTG
{F_Caps} .ATCAGTTTT .GACCGTTGG ATAAAGGCAG GAAGAATGTA GCACTC.TCG GGTGAACTTA TAGCTTCTTG
{F_Unig} .ATCAGTTTT .GATCGCTGG ATAAAGGCAG GAGGAATGTA GCACCC.CCG GGTGAACTTA TAGCTTCTTG
{C_Neob} .ATCAGTTCT .GATCGGTGG ATAAGGGCTG GAGGAATGTG GCACTCTTCG GGGTGTGTTA TAGCCTCCTG
{F_Neoc} .ATCAGTTCT .GATCGGTGG ATAAGGGCTG GAGGAATGTG GCACTCTTCG GGGTGTGTTA TAGCCTCCTG
{F_Neod} .ATCAGTTCT .GATCGGTGG ATAAGGGCTG GAGGAATGTG GCACTCTTCG GGGTGTGTTA TAGCCTCCTG
{C_Neof} .ATCAGTTCT .GATCGGTGG ATAAGGGCTG GAGGAATGTG GCACTCTTCG GAGTGTGTTA TAGCCTCCTG
{T_Beig} .ATCAGTTTT .GTCCGGTGG ATAAAGGTAG TAGGAATGTG ..ACTTCTCC GGAAGTGTTA TAGCCTATTA
{C_Laur} .ATCAGTTTT .GTCCGACGG ATAATGGCGG CGGGAAAGTA GCAC..CTCC GGGTGTGTTA TAGCCCGCTG
{Beauve} .ATCAGTTCG CCCT.GGGGG ACAAAGGCTT CGGGAACGTG GCTCTCTCC. .....GGGGA ..........
{Fusari} .ATCAGTTCG CSOC.GGGGG ATAAAGRCTT CGGGAATGTG GCTCYCYYC. .....GGGGA ..........
{Acremo} .ATCAGTTCG CGCC.GGGGG ATAAAGGTTT CGGGAATGTA GCTCCTTC.. ......GGGA ..........
{Paecil} .ATCAGTTCG CCGC.GGGGG AAAAAGGCTT CGGGAACGTG GCTCCTAC.. ......GGGA ..........
{P_Boyd} .ATCAGTTCG CTGCAGGGGG AGAAAGGCGA TGGGAATGTG GCTC..TTC. ........GGA ..........
{S_Brum} .ATCAGTTCG CCTCGGGGGG AGAAAGGCGG CGGGAATGTG GCTC..TAC. ........GGA ..........
{S_Brev} .ATCAGTTCG .TCCGGGGGG AGAAAGGCGG CGGGAATGTG GCTC..TTC. ........GGA ..........
{Sporot} .ATCGGTTCT C.CCAGGGGG ACAAAGGCCG CGGGAACGTA GCTCCTTCG. ........GGA ..........
{B_Derm} .GTCGGTTTC .GACGGCCGG TCAAAGGCCC CCGGAATGTG TCGCCTCTC. .....GGGG.C ..........
{H_Caps} .GTCGGTTTC .GACGGCCGG TCAAAGGCCC CCGGAATGTG TCGCCTCTC. .....GGGG.C ..........
{A_Nidu} .GTCGGTTTG .GGCGGCCGG TCAAAGGCCC CAGGAATGTA TCGCCCTCC. .....GGGGTT ..........
{A_Ungu} .GTCGGTTTG .GGCGGCCGG TCAAAGGCCC CAGGAATGTA TCACCCTCC. .....GGGGTT ..........
{A_Ustu} .GTCGGTTTG .GGCGGCCGG TCAAAGGCCC CAGGAATGTG TCGCCCTCC. .....GGGG.C ..........
{A_Clav} .GTCGGTTTG .GGCGGCCGG TCAAAGGCCT CCGGAATGTA TCACCTCTC. .....GGGG.T ..........
{A_Fumi} .GTCGGTTTG .GGCGGCCGG TCAAAGGCCC TCGGAATGTA TCACCTCTC. .....GGGG.T ..........
{A_Flav} .GTCGGTTTG .GGCGGCCGG TCAAAGGCTC CCGGAATGTA GTGCCCTYC. .....GGGG.C ..........
{A_Ochr} .GTCGGTTTG .GGCGGCCGG TCAAAGGCCC CCGGAATGTA GCACCCTTC. .....GGGG.T ..........
{A_Nige} .GTCGGTTTG .GGCGGCCGG TCAAAGGCCC CTGGAATGTA GTRCCCTCC. .....GGGG.Y ..........
{A_Terr} .GTCGGTTTG .GGCGGCCGG TCAAAGGCCT CCGGAATGTA GCGCCCTC.. .....GGGG.C ..........
{A_Glau} .GTCGGTTTG .GGCGGCCGG TCAAAGGCCC CTGGAATGTA ACGCCTCTC. .....GGGG.C ..........
{Penici} .GTCGGTTTG .GACGGCCGG TCAAAGGCCC TCGGAATRTA ACGCCCCC. .....GGGG.C ..........
{C_Immi} .ATCAGTTCT .GGCGGTTGG TTAAAGGCCT CTGGAATGTA TCGTCCTCC. ......GGGAC ..........
{Bipola} .ATCAGTTTG .GGCGGTGGG ATAAAGGTCT CTGTCACGTA CTTTCCTTC. .....GGGTTG ..........
{Curvul} .ATCAGTTTG .GGCGGTGGG ATAAAGGTCT CTGACACGTT CCTTCCTTC. .....GGGTTG ..........
{Chryso} .ATCGGTTTT .GGCGGCTGG ATAAAGGCCC TAGGAATGTG GCTCCTCTC. .....GGGGAG ..........
{Clados} .ATCGTCTGG .TGCCGCTGG AT.AAGACTT GAGGAATGTA GCTCCCTCG. .....GGAGTG ..........
{Malbra} .ATCAGTTTT .GGCGGCCGG TCAAAGGCCC TTGGAATGTA TCGTCCTCC. ....GGG.AC ..........
{C_Para} .ATCAGTTT. .GAGCGGTAG GATAAGTGCA AAGAAATGTG GCACTGCTTC ....GGTAGT ..........
{C_Trop} .ATCAGTTT. .GGGCGGTAG GAGAATTGCG TTGGAATGTG GCACGGCTTC ....GGTTGT ..........
{C_Albi} .ATCGGTTTG .GAGCGGCAG GATAATGGCG GAGGAATGTG GCACGGCTTC ....TGCTGT ..........
{C_Guil} .ATCGGTTT. .GGGCGGTAG GATAATGGCG TAGGAATGTG ACTTTRCTTC ....GGTGAA ..........
{C_Glab} .ATCGGTTTT .G.GCGGCCG GAAAAAACCT AGGGAATGTG GCTCTGCGCC TCGGTGTAGA ..........
{S_Cere} .ATCAGTTTT .G.GTGGCAG GATAAATCCA TAGGAATGTA GCTTGCCTC. .....GGTAA ..........
{C_Kefy} .ATCAGTTTT .A.GCGGTTG GATAAATCCT CGGGAATGTG GCTCTGCTTC ....GGTAGA ..........
{Geotri} .TGGGGTGTT .TGGGAGT.. GAAAAAGAAG TAGGAACGTA ACTCTTC... ........GGA ..........
{C_Lusi} .GTC.GAAAA .GGGGGGAGG AACAAGAACT CGAGAATGTG GCGCGCACCT TCGGGYGCGC ..........
{C_Krus} .ATCGGTTCT .TGCTGCAGG AGAAGGGGTT CTGGAACGTG GCTCTTC... .......GGA ..........
{Blasch} .......... .......... .......... .......... .......... .......... ..........
{P_Braz} GCGTCGGTTT CGACGGCCGG TCAAAGGCCC CCGGAATGTG TC...GCCTC TCGGGG.... ..........
{Pc_Hum} GCATCGGTTT CAGTTACTGG ATAAAACTGG AAGAAGGTAG GCTCTCTTCG GAGGGTTTTT TAGCTTCCAG
         141                                                                     210
{Rhizo2} CCTTAGAAAA TACCTTGGGT TGGATTGAGG AACGCAGCGA ATG....... .......... ...CTTATTG
{Rhizo3} CCTTAGAAAA TACCTTGGGC TGGATTGAGG TACGCAGCGA ATG....... .......... ...CTATTTG
{Rhizo1} CTTTAGAAAA TACCTTGAAT TGGATTGAGG AACGCAGCGA ATGCTTCTCT TTAGAGGCAA AGTCTTTTAT
{Mucor_} CCTACTATCA TACTCTGGAT TGGACTGAGG AACGCAGCGA ATGCCWTTAG GCRAGATTGC TGGGTGCTTT
```

TABLE 3-continued

Multiple Sequence alignment for (SEQ ID NO: 24) through (SEQ ID NO: 74), (SEQ ID NO: 77) AND (SEQ ID NO: 78)

```
{C_Terr} TCGTATACAG TGGTTGGGAC TGAGGAACGC AGCATGCCTT TATGGCCGGG GTTCGCCCAC GTACATGCTT
{F_Caps} TCACATACAA TGGTTGGGAC TGAGGAACCC AGCATGCCTT TATGGCCGGG ATTCGTCCAC GTACATGCTT
{F_Unig} TCACATACAG TGGTTGGGAC TGAGGAACGC AGCATGCCTT TATGGCCGGG ATTCGTCCAC GTACATGCTT
{C_Neob} TCGCATACAC TGGTTGGGAC TGAGGAATGC AGCTCGCCTT TATGGCCGGG GTTCGCCCAC GTTCGAGCTT
{F_Neoc} TCGCATACAC TGGTTGGGAC TGAGGAATGC AGCTCGCCTT TATGGCCGGG GTTCGCCCAC GTTCGAGCTT
{F_Neod} TCGCATACAC TGGTTGGGAC TGAGGAATGC AGCTCGCCTT TATGGCCGGG GTTCGCCCAC GTTCGAGCTT
{C_Neof} TCGCATACAC TGGTTGGGAC TGAGGAATGC AGCTCGCCTT TATGGCCGGG GTTCGCCCAC GTTCGAGCTT
{T_Beig} TCACATACAC TGGGTGAGAC TGAGGACTGC AGCTCGCCTT TATGGCCGGG CTTCGGGCAC GTTCGAGCTT
{C_Laur} TCGCATACGC CGGATGAGAC TGAGGCATGC AGCTCGCCTT TATGGCAGGG GTTCGCCCAC TTTCGAGCTT
{Beauve} .........G TGTTATAGCC CGTTGCGTAA TACC.CTGTG GCGGACTGAG GTTCGCG... ..CATTCGCA
{Fusari} .........G TGTTATAGCC CGTTGYSTAA TACC.CTGGB GGGGACTGAG GTTCGCG... ..CWTCTGCA
{Acremo} .........G TGTTATAGCC CGTTGCGTAA TACC.CTGGC GTGGACTGAG GTCCGCG... ...C.TCTGCA
{Paecil} .........G TGTTATAGCC CGTTGCATAA TACC.CTGGG GCGGACTGAG GTTCGCG... ...C.TCCGCA
{P_Boyd} .........G TGTTATAGCC CGCCGCGCAA TACC.CCTCG GCGGACTGAG GACCGCG... ..CATCTGCA
{S_Brum} .........G TGTTATAGCC CGCCGCGTAA TACC.CCCGG GCGGACTGAG GACCGCG... ..CGTATGCA
{S_Brev} .........G TGTTATAGCC CGCCGTCTAA TACC.CTCGG GTGGACTGAG GACCGCG... ..CGTATGCA
{Sporot} .........G TGTTATAGCC CGCGGCGGCA TGCC.CCTGG GGGGACCGAG GACCGCG... ..CTTCGGCA
{B_Derm} .........G TCTTATAGCC GGGGGTGCAA TGCGGCCAGT CGGGACCGAG GAACGCG... ..CTTCGGCA
{H_Caps} .........G TCTTATAGCC GGGGGTGCAA TGCGGCCAGT CGGGACCGAG GAACGCG... ..CTCCGGCA
{A_Nidu} .........G TCTTATAGCC TGGGGTGCAA TGCGGCCAGC CCGGACCGAG GAACGCG... ..CTTCGGCA
{A_Ungu} .........G TCTTATAGCC TGGGGTGCAA TGCGGCCAGC CTGGACCGAG GAACGCG... ..CTTCGGCA
{A_Ustu} .........G TCTTATAGCC TGGGGTGCAA TGCGGCCAGC CCGGACCGAG GAACGCG... ..CTTCGGCA
{A_Clav} .........G TCTTATAGCC GGGGGTGCAA TGCGGCCTGC CTGGACCGAG GAACGCG... ..CTTCGGCT
{A_Fumi} .........G TCTTATAGCC GAGGGTGCAA TGCGGCCTGC CTGGACCGAG GAACGCG... ..CTTCGGCT
{A_Flav} .........A CCTTATAGCC GGGAGTGCAA TGCGGCCAGC CTGGACCGAG GAACGCG... ..CTTCGGCA
{A_Ochr} .........G CCTTATAGCC GGGGGTGCAA TGCGGCCAGC CTGGACCGAG GAACGCG... ..CTTCGGCA
{A_Nige} .........A CCTTATAGCC AGGGGTGCAA TGCGGCCAGC CTGGACCGAG GAACGCG... ..CTTCGGCA
{A_Terr} .........G CCTTATAGCC GGGGGTGCAA TGCGGCCAGC CTGGACCGAG GAACGCG... ..CTTCGGCA
{A_Glau} .........G CCTTATAGCC AGGGGTGTCA TGCGGCCAGC CTGGACCGAG GAACGCG... ..CTTCGGCA
{Penici} .........G TCTTATAGCC GAGGGTGCCA TGCGGCCAGC MCAGACCGAG GAACGCG... ..CTTCGGCT
{C_Immi} .........G TCTTATAGCC AGGGGCGCAA TGCGGCCAGC CGGGACCGAG GAACGCG... ..CTTCGGCA
{Bipola} .........G CCATATAG.G GGAGACGTCA TACCACCAGC CTGGACTGAG GTCCGCG... ..CATCTGCT
{Curvul} .........G CCATATAG.G GGAGACGTCA TACCACCAGC CTGGACTGAG GTCCGCG... ..CATCTGCT
{Chryso} .........T GTTATAGC.C TAGGGTGCAA TGCAGCCTGC TGGGACCGAG GACCGCG... ..CTTCGGCT
{Clados} .......... ...TTATA.G CCTCTTGTGA TGCAGCGAGC GCCGGGCGAG GTCCGCG... ..CTTCGGCT
{Malbra} .........G TCTTATAGCC AAGGGTGCAA TGCGGCCAGC CGGGACTGAG GAACGCG... ..CTTCGGCA
{C_Para} .........G TGTTATAGTC T.TTGTC.GA TACTGCCAGC TTAGACTGAG GACTGCG..G CTTCG.GCCT
{C_Trop} .........G TGTTATAGCC T.TCGTC.GA TACTGCCAGC CTAGACTGAG GACTGCG..G TTTAT.ACCT
{C_Albi} .........G TGTTATAGCC T.CTGAC.GA TGCTGCCAGC CTAGACCGAG GACTGCG..G TTTTTAACCT
{C_Guil} .........G TGTTATAGCC T.GCGTT.GA TGCTGCCTGC CTAGACCGAG GACTGCG..A TTTT..ATCA
{C_Glab} .........G TGTTATAGCC C.TGGGG.AA TACGGCCAGC CGGGACCGAG GACTGCGATA CTTGTTATCT
{S_Cere} .........G TATTATAGCC T.GTGGG.AA TACTGCCAGC TGGGACTGAG GACTGCGACG TAAG...TCA
{C_Kefy} .........G TGTTATAGCC C.GTGGG.AA TACAGCCAGC TGGGACTGAG GATTGCGACT TTTG...TCA
{Geotri} .........G TGTTATAGCC T.ACTTT.CA TAGCTCCTCA GGCGCCTCAG GACTGPG... ..CTTCGGCA
{C_Lusi} .........G TGTTATAGCT C.GTGTT..GA CGCCTCCATC CCTTTTCGAG GCCTGCGAT. .......TCT
{C_Krus} .........G TGTTATAGCC A.GGGCCAGA TGCTGCCTGC GGGGACCGAG GACTGCGGCC GTGTAGGTCA
{Blasch} .....TGAAA TTGTTGAAAG GGAAGGCGAT GGTAGGAATA AGAGGCTGCG GTTTGAAATA ATTGTTTTTC
{P_Braz} ........CG TCTTATAGCC GGGGGTGCAA TGCGGCCAGT CGGGACCGAG GAACGCGCT. ....CCGGCA
{Pc_Hum} TAGCTGCAGT GACCGGGACC GGAAGGGAAA TTGGGTCTTT GAAGACCTTA TGATGTTGGC AGAAATGGTC
         211                                                      250
```

```
{Rhizo2} GCGAGTTTTC CAGGAAGGT. .....TTTCT GAGGTACTAC                      SEQ ID NO: 68
{Rhizo3} GCGAGTTGGC TGGGAATAT. .....TTTCT GAGGTGCTTT                      SEQ ID NO: 69
{Rhizo1} TGGGATTTAC GGATCAGAC. .....TGTGG CATTGTCACA                      SEQ ID NO: 67
{Mucor_} CGCTAATAAA TGTTAGAATT TCTGCTTCGG GTGGTGCTAA                      SEQ ID NO: 63
{C_Terr} AGG..ATGTT GACATAATGG CTTTAAACGA CCCGTCTTGA                      SEQ ID NO: 53
{F_Caps} AGG..ATGTT GACATAATGG CTTTAAACGA CCCGTCTTGA                      SEQ ID NO: 56
{F_Unig} AGG..ATGTT GACATAATGG CTTTAAACGA CCCGTCTTGA                      SEQ ID NO: 59
{C_Neob} AGG..ATGTT GACAAAATGG CTTTAAACGA CCCGTCTTGA                      SEQ ID NO: 50
{F_Neoc} AGG..ATGTT GACAAAATGG CTTTAAACGA CCCGTCTTGA                      SEQ ID NO: 57
{F_Neod} AGG..ATGTT GACAAAATGG CTTTAAACGA CCCGTCTTGA                      SEQ ID NO: 58
{C_Neof} AGG..ATGTT GACAAAATGG CTTTAAACGA CCCGTCTTGA                      SEQ ID NO: 51
{T_Beig} AGG..ATGTT GACATAATGG CTTTAAACGA CCCGTCTTGA                      SEQ ID NO: 74
{C_Laur} AGG..ATGTT GACGTAATGG CTTTAAACGA CCCGTCTTGA                      SEQ ID NO: 48
{Beauve} AGG..ATGCT GGCGTAATGG TCATCAGTGA CCCGTCT...                      SEQ ID NO: 35
{Fusari} AGG..ATGCT GGCGTAATGG TCATCAACGA CCCGTCTTGA                      SEQ ID NO: 55
{Acremo} AGG..ATGCT GGCGTAATGG TCATCAGTGA CCCGTCTTGA                      SEQ ID NO: 24
{Paecil} AGG..ATGCT GGCGTAATGG TCATCAGCGA CCCGTCTTGA                      SEQ ID NO: 64
{P_Boyd} AGG..ATGCT GGCGTAATGG TCGTCAGCGA CCCGTCTTGA                      SEQ ID NO: 66
{S_Brum} AGG..ATGCT GGCGTAATGG TCGTCAGCGA CCCGTCTTGA                      SEQ ID NO: 72
{S_Brev} AGG..ATGCT GGCGTAATGG TCGTCAGCGA CCCGTCTTGA                      SEQ ID NO: 71
{Sporot} AGG..ATGCT GGCGTAATGG TCACCAGCGA ACCGTCTTGA                      SEQ ID NO: 70
{B_Derm} CGG..ACGCT GGCTTAATGG TCGTAAGCGA CCCGTCTTGA                      SEQ ID NO: 38
{H_Caps} CGG..ACGCT GGCTTAATGG TCGTCAGCGA CCCGTCTTGA                      SEQ ID NO: 61
{A_Nidu} CGG..ACGCT GGCGTAATGG TCGCAAACGA CCCGTCTTGA                      SEQ ID NO: 29
{A_Ungu} CGG..ACGCT GGCATAATGG TTGCAAACGA CCCGTCTTGA                      SEQ ID NO: 33
{A_Ustu} CGG..ACGCT GGCGTAATGG TCGCAAACGA CCCGTCTTGA                      SEQ ID NO: 34
```

TABLE 3-continued

Multiple Sequence alignment for (SEQ ID NO: 24) through
(SEQ ID NO: 74), (SEQ ID NO: 77) AND (SEQ ID NO: 78)

| | | | | | |
|---|---|---|---|---|---|
| {A_Clav} | CGG..ACGCT | GGCGTAATGG | TCGTAAATGA | CCCGTCTTGA | SEQ ID NO: 25 |
| {A_Fumi} | CGG..ACGCT | GGCGTAATGG | TCGTAAATGA | CCCGTCTTGA | SEQ ID NO: 27 |
| {A_Flav} | CGG..ACGCT | GGCATAATGG | TCGYAAACGA | CCCGTCTTGA | SEQ ID NO: 26 |
| {A_Pchr} | CGG..ACGCT | GGCATAATGG | TCGTAAACGA | CCCGTCTTGA | SEQ ID NO: 31 |
| {A_Nige} | CGG..ACGCT | GGCATAATGG | TCGTAAACGA | CCCGTCTTGA | SEQ ID NO: 30 |
| {A_Terr} | CGG..ACGCT | GGCATAATGG | TTGTAAACGA | CCCGTCTTGA | SEQ ID NO: 32 |
| {A_Glau} | CGG..ACGCT | GGCATAATGG | TCGTAAACGA | CCCGTCTTGA | SEQ ID NO: 28 |
| {Penici} | CGG..ACGCT | GGCATAATGG | TCGTAAA... | .......... | SEQ ID NO: 65 |
| {C_Immi} | CGG..ATGCT | GGCATAATGG | TTGTAAGCGG | CCCGTCTTGA | SEQ ID NO: 45 |
| {Bipola} | AGG..ATGCT | GGCGTAATGG | CTGTAAGCGG | CCCGTCTTGA | SEQ ID NO: 36 |
| {Curvul} | AGG..ATGCT | GGCGTAATGG | CTGTAAGCGG | CCCGTCTTGA | SEQ ID NO: 41 |
| {Chryso} | AGG..ATGCT | GGCGTAATGG | TTGTAAGCGG | CCCGTCTTGA | SEQ ID NO: 39 |
| {Clados} | AGG..ATGCT | GGCGTAATGG | TCGTAATCCG | CCCGTCTTGA | SEQ ID NO: 40 |
| {Malbra} | CGG..ATGCT | GGCGTAATGG | CTGTAAGCGG | CCCGTCTTGA | SEQ ID NO: 62 |
| {C_Para} | AGG..ATGTT | GGCATAATGA | TCTTAAGTCG | CCCGTCTTGA | SEQ ID NO: 52 |
| {C_Trop} | AGG..ATGTT | GGCATAATGA | TCTTAAGTCG | CCCGTCTTGA | SEQ ID NO: 54 |
| {C_Albi} | AGG..ATGTT | GGCATAATGA | TCTTAAGTCG | CCCGTCTTGA | SEQ ID NO: 42 |
| {C_Guil} | AGG..ATGCT | GGCATAATGA | TCCCAAACCG | CCCGTCTTGA | SEQ ID NO: 44 |
| {C_Glab} | AGG..ATGCT | GGCATAATGG | TTATATGCCG | CCCGTCTTGA | SEQ ID NO: 43 |
| {S_Cere} | AGG..ATGCT | GGCATAATGG | TTATATGCCG | CCCGTCTTGA | SEQ ID NO: 73 |
| {C_Kefy} | AGG..ATGCT | GGCGTAATGG | TTAAATGCCG | CCCGTCTTGA | SEQ ID NO: 46 |
| {Geotri} | AGG..ACCTT | GGCATAATGA | TTCTATACCG | CCCGTCTTGA | SEQ ID NO: 60 |
| {C_Lusi} | AGG..ACGCT | GGCGTAATGG | TTGCAAGCCG | CCCGTCTTGA | SEQ ID NO: 49 |
| {C_Krus} | CGG..ATGCT | GGCAGAACGG | CGCAACACCG | CCCGTCTTGA | SEQ ID NO: 47 |
| {Blasch} | GGGCCACGGT | CTCCTGAGCC | TGCTTTCGCA | CCCGTCTTGA | SEQ ID NO: 37 |
| {P_Braz} | CGG..ACGCT | GGCTTAATGG | TCGTAAGCGA | CCCGTCTTG~ | SEQ ID NO: 77 |
| {Pc_Hum} | CTAAGCGACC | CGTCTTGAAA | CACGGACCAA | GGAGTCTAAT | SEQ ID NO: 78 |

Legend to Table 3:

The multiple sequence alignment shows the sequence of 28S ribosomal RNA genes amplified with primers SEQ ID NO: 1 and SEQ ID NO: 2. 23 species specific probes (SEQ ID NO: 3 to SEQ ID NO: 23, SEQ ID NO: 75 and SEQ ID NO: 76) are shown underlined. Minor sequence variation among two isolate of the same organism are represented by the appropriate code (see key below). Major differences among Rhizopus species are depicted by including 3 separate Rhizopus sequences in the alignment. (The organisms in this figure are listed according to their sequence relatedness.)
Key to symbols:
- (.) gap in sequence to facilitate alignment
- (R) A or G
- (W) A or T
- (Y) T or C
- (M) A or C
- (K) T or G
- (S) G or C
- (B) T, G or C

| | |
|---|---|
| Acremo | Acremonium species |
| A_clav | Aspergillus clavatus |
| A_flav | Aspergillus flavus |
| A_fumi | Aspergillus fumigarus |
| A_glau | Aspergillus glaucus |
| A_nidu | Aspergillus nidulans |
| A_nige | Aspergillus niger |
| A_ochr | Aspergillus ochraceus |
| A_terr | Aspergillus terreus |
| A_ungu | Aspergillus unguis |
| A_ustu | Aspergillus ustus |
| Beauve | Beauveria species |
| Bipola | Bipolaris species |
| Blasch | Blastoschizomyces species |
| B_derm | Blastomyces dermatitidis |
| Chryso | Chrysosporium species |
| Clados | Cladosporium species |
| Curvul | Curvularia species |
| C_albi | Candida albicans |
| C_glab | Candida glabrata |
| C_guil | Candida guilliermondii |
| C_immi | Coccidioides immitis |
| C_kefy | Candida kefyr |
| C_krus | Candida krusei |
| C_laur | Cryptococcus laurentii |
| C_lusi | Candida lusitaniae |
| C_neob | Cryptococcus neoformans var gattii serotype B |
| C_neof | Cryptococcus neoformans serotype A |
| C_para | Candida parapsilosis |
| C_terr | Cryptococcus terreus |
| C_trop | Candida tropicalis |
| Fusari | Fusarium species |
| F_caps | Filobasidium capsuligenum |
| F_neoc | Filobasidiella (Cryptococcus) neoformans var bacillispora serotype C |
| F_neod | Filobasidiella (Cryptococcus) neoformans var neoformans serotype D |
| F_unig | Filobasidium uniguttulatum |
| Geotri | Geotrichum species |
| H_caps | Histoplasma capsulatum |
| Malbra | Malbranchea species |
| Mucor_ | Mucor species |
| Paecil | Paecilomyces species |
| Penici | Penicillium species |
| P_boyd | Pseudallescheria boydii |
| P_braz | Paracoccidioides brasiliensis |
| Pc-Hum | Pneumocystis carinii, human isolate |
| Rhizo1 | Rhizopus species isolate #1 |
| Rhizo2 | Rhizopus species isolate #2 |
| Rhizo3 | Rhizopus species isolate #3 |
| Sporot | Sporothrix schenkii |
| S_brev | Scopulariopsis brevicaulis |
| S_brum | Scopulariopsis brumpti |
| S_cere | Saccharomyces cerevisiae |
| T_beig | Trichosporon beigelii |
| | Pneumocystis carinii |

Further variations of the invention that utilize any of the named sequences will be apparent to those with ordinary skill in the art. The following examples illustrate various aspects of the invention but are not intended to limit its usefulness.

EXAMPLE 1

Testing probes SEQ ID NO: 3 to SEQ ID NO: 23, SEQ ID NO: 75 and SEQ ID NO: 76 for hybridization specificity Probes listed in SEQ ID NO: 3 to SEQ ID NO: 23, SEQ ID NO: 75 and SEQ ID NO: 76 were tested for specificity against their target organisms. Probe SEQ ID NO: 5 for *Candida albicans* was the first one tested against a panel of fungi taken from the Mayo Clinic collection. 28S rDNA from Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergillus ustus*, Aspergillus sp., Beauvaria sp., Bipolaris sp., *Blastomyces dermatitidis, Candida albicans, Candida glabrata, Candida guilliermondii, Candida kefyr, Candida krusei, Candida lusitaniae, Candida parapsilosis, Candida tropicalis*, Chrysosporium sp., Cladosporium sp., *Coccidioides immitis, Cryptococcus neoformans* serotype A, Curvularia sp., Fusarium sp., Geotrichum sp., *Histoplasma capsulatum*, Mucor sp., Penicillium sp., *Pseudallescheria boydii*, Rhizopus sp., *Saccharomyces cerevisiae, Scopulariopsis brevicaulis, Sporothrix schenkii* and *Trichosporon beigelii* was amplified in a polymerase chain reaction using oligonucleotide probes SEQ ID NO: 1 and SEQ ID NO: 2. All PCR amplifications were carried out as hot-start reactions in a 50 ul reaction volume using Perkin-Elmer (Norwalk, Conn.) 0.5 ml thin-wall polypropylene tubes and a Perkin-Elmer thermal cycler. Reagents added to the tube initially were 2.5 ul of 10× PCR buffer (100 mM tris pH 8.3, 500 mM KCl, 15 mM $MgCl_2$), 5.0 ul of 50% glycerol/1 mM cresol red, 8.0 ul of dNTP mix (1.25 mM each of DATP, dGTP, dTTP and dCTP), 11 picomoles of each nucleic acid primer and sterile water to make up a volume of 25 ul. A wax bead (Ampliwax Gem=100, Perkin-Elmer) was added and the tubes heated to 77° C. for 30 seconds and cooled to room temperature to form a wax barrier. 2.5 ul of 10× PCR buffer, 5.0 ul of 50% glycerol/1 mM cresol red, 0.2 ul Taq polymerase (AmpliTaq 5U/ul, Perkin-Elmer) and 15.3 ul of sterile water was added to the tube along with 2.0 ul of DNA from the fungal whole cell boiled lysate described above. 50 cycles of thermal cycling was carried out at 94° C.—30 sec, 50° C.—1 min, 72° C.—2 min. Five microliters of polymerase chain reaction mix from each sample was run on a 5% polyacrylamide gel to visually confirm the successful amplification of 28S rDNA from each fungus listed above. 40 ul of the remaining amplified 28S rDNA was denatured in 1 N NaOH, and half of this denatured rDNA was slot blotted on to a positively charged polysulphone based membrane equilibrated in 0.5 N NaOH. The membrane was air dried for 15 minutes and baked in a vacuum oven at 80° C. for 30 minutes. Amplified rDNA from each species was now bound and immobilized at a separate spot on the membrane. The free binding sites on the membrane were blocked by incubating the membrane for 3 hours at 40° C. in hybridization buffer (100 ml of hybridization buffer was made using 1 g non-fat milk powder, 6 g $NaH_2PO_4$, 7 g SDS, 200 ul 0.5M EDTA and adjusted to pH 7.2 with NaOH). The specific probe for *Candida albicans* (SEQ ID NO: 5) was end-labeled with radioactive phosphorus using $^{32}P$ ATP and T4 polynucleotide kinase. 50 picomoles of this probe was added to 70 milliliters of hybridization buffer and the membrane was probed at 40° C. overnight. The membrane was washed in hybridization buffer at 40° C. for 15 minutes followed by a wash in 2× SSC at 40° C. for 15 minutes. The membrane was then exposed on x-ray film for at least 1 hour. The oligonucleotide probe SEQ ID NO: 5 only hybridized to amplified 28S rDNA from *Candida albicans* (see Table 4) Under these hybridization conditions, probe SEQ ID NO: 5 is extremely specific for *Candida albicans*. The sequence of oligonucleotide probe SEQ ID NO: 5 differs from the sequences of other species of Candida by as few as 1 or 2 bases, but these mismatches are sufficient to prevent stable hybrids from forming with the other Candida species.

Probes SEQ ID NO: 3 to SEQ ID NO: 23 were tested for specificity, as described above for the *Candida albicans* probe SEQ ID NO: 5, against the same panel of fungi listed in the preceding paragraph. The positively charged polysulphone based membrane probed with *Candida albicans* probe SEQ ID NO: 5 was washed in 0.5 N NaOH at 40° C. for 10 minutes to remove all bound *Candida albicans* probe. The membrane was sequentially probed with all probes listed in SEQ ID NO: 3 to SEQ ID NO: 23. For each subsequently tested probe, the membrane was blocked for at least 30 minutes, probe hybridization was carried out at 40–42° C. for at least 3 hours, and post-hybridization washes were done in 2× SSC for 20 minutes. The membrane was stripped between probings by washing in 0.5 to 1.0 N NaOH at 40–42° C. Results are listed in Tables 4 to 7.

Probes SEQ ID NO: 75 and SEQ ID NO: 76 were tested for specificity against a modified panel of fungi, using the procedure just described. The specific organisms tested and the results obtained are listed in Table 8.

As shown in Tables 4 to 8, each probe listed in SEQ ID NO: 3 to SEQ ID NO: 23, SEQ ID NO: 75 and SEQ ID NO: 76 specifically hybridizes to only one target fungal 28S nucleic acid sequence. This specificity is essential for identifying a given species of fungus in clinical specimens containing mixed fungal organisms with a high level of reliability. The organisms listed in these Tables represent a majority of organisms that are commonly isolated from clinical samples. While we have developed 23 species specific probes (SEQ ID NO: 3 to SEQ ID NO: 23, SEQ ID NO: 75 and SEQ ID NO: 76) that identify a total of 21 individual organisms, the additional organisms listed in the test panel were used to ensure that our probes did not have any cross-reactivity with other fungi likely to be present in a clinical specimen. The ability to accurately and reliably diagnose, and identify to a species level, this large a number of pathogens is unmatched by any other report. The fact that we can achieve this by probing DNA amplified by a single pair of "Universal" probes (SEQ ID NO: 1 and SEQ ID NO: 2) is highly advantageous as it saves time, money and effort by providing the ability to test a single amplified target with 23 different probes (SEQ ID NO: 3 to SEQ ID NO: 23, SEQ ID NO: 75 and SEQ ID NO: 76).

A GenBank search was carried out with all probes listed in SEQ ID NO: 3 to SEQ ID NO: 23, SEQ ID NO: 75 and SEQ ID NO: 76 in order to determine whether similar gene sequences were present in the database. 28S sequences for *Candida albicans Cryptococcus neoformans* are already present in GenBank, and as expected, the probes for *Candida albicans* and *Cryptococcus neoformans* correctly identified the 28S sequences from these two organisms. Ten other probes also matched DNA sequences from a variety of genes not related to the 28S gene (Table 9). This was expected because short stretches of sequence identity can often be found for any query sequence in unrelated genes from the same or a different organism. This observation is known to those versed in this art. In all cases, sequences that matched a probe sequence were not located within the 28S rRNA genes. Our probes are used to analyze 28S DNA that has been previously amplified in a polymerase chain reaction with our probes SEQ ID NO: 1 and SEQ ID NO: 2. Under stringent conditions, these two probes only amplify DNA from fungal 28S rRNA genes. Therefore no amplified DNA from the non-28S genes listed in Table 9 will be available for the hybridization of probes SEQ ID NO: 3 to SEQ ID NO: 23. The presence of related sequences in non-28S, unamplified genes will not be detected and will, thus, not have any effect on the sensitivity or the specificity of our detection and identification strategy.

TABLE 4

Detection of species specific 28S sequence with probes SEQ ID NO: 3 to SEQ ID NO: 8

| FUNGUS | SEQ ID: 3 | SEQ ID: 4 | SEQ ID: 5 | SEQ ID: 6 | SEQ ID: 7 | SEQ ID: 8 |
|---|---|---|---|---|---|---|
| Acremonium sp. | − | − | − | − | − | − |
| Aspergillus clavatus | − | − | − | − | − | − |
| Aspergillus flavus | − | − | − | − | − | − |
| Aspergillus fumigatus | + | − | − | − | − | − |
| Aspergillus glaucus | − | − | − | − | − | − |
| Aspergillus nidulans | − | − | − | − | − | − |
| Aspergillus niger | − | − | − | − | − | − |
| Aspergillus ochraceus | − | − | − | − | − | − |
| Aspergillus terreus | − | − | − | − | − | − |
| Aspergillus unguis | − | − | − | − | − | − |
| Aspergillus ustus | − | − | − | − | − | − |
| Aspergillus sp. | − | − | − | − | − | − |
| Beauvaria sp. | − | − | − | − | − | − |
| Bipolaris sp. | − | − | − | − | − | − |
| Blastomyces dermatitidis | − | − | − | − | − | − |
| Candida albicans | − | − | + | − | − | − |
| Candida glabrata | − | − | − | − | − | − |
| Candida guilliermondii | − | − | − | − | − | − |
| Candida kefyr | − | − | − | − | − | − |
| Candida krusei | − | − | − | − | − | − |
| Candida lusitaniae | − | − | − | − | − | − |
| Candida parapsilosis | − | − | − | − | − | − |
| Candida tropicalis | − | − | − | − | − | − |
| Chrysosporium sp. | − | − | − | − | − | − |
| Cladosporium sp. | − | − | − | − | − | − |
| Coccidioides immitis | − | − | − | + | − | − |
| Cryptococcus neoformans | − | − | − | − | + | + |
| Curvularia sp. | − | − | − | − | − | − |
| Fusarium sp. | − | − | − | − | − | − |
| Geotrichum sp. | − | − | − | − | − | − |
| Histoplasma capsulatum | − | − | − | − | − | − |
| Mucor sp. | − | − | − | − | − | − |
| Penicillium sp. | − | − | − | − | − | − |
| Pseudallescheria boydii | − | − | − | − | − | − |
| P. brasiliensis | − | − | − | − | − | − |
| Pneumocystis carinii | − | − | − | − | − | − |
| Rhizopus sp. | − | − | − | − | − | − |
| Saccharomyces cerevisiae | − | − | − | − | − | − |
| Scopulariopsis brevicaulis | − | − | − | − | − | − |
| Sporothrix schenckii | − | − | − | − | − | − |
| Trichosporon beigelii | − | − | − | − | − | − |

+ Positive
− Negative after 20 minute wash in 2X SSC

TABLE 5

Detection of species specific 28S sequence with probes SEQ ID NO: 9 to SEQ ID NO: 14

| FUNGUS | SEQ ID: 9 | SEQ ID: 10 | SEQ ID: 11 | SEQ ID: 12 | SEQ ID: 13 | SEQ ID: 14 |
|---|---|---|---|---|---|---|
| Acremonium sp. | − | − | − | − | − | − |
| Aspergillus clavatus | − | − | − | − | − | − |
| Aspergillus flavus | − | − | − | − | − | − |
| Aspergillus fumigatus | − | − | − | − | − | − |
| Aspergillus glaucus | − | + | − | − | − | − |
| Aspergillus nidulans | − | − | − | − | − | − |
| Aspergillus niger | − | − | + | − | − | − |
| Aspergillus ochraceus | − | − | − | − | − | − |
| Aspergillus terreus | − | − | − | + | − | − |
| Aspergillus unguis | − | − | − | − | − | − |
| Aspergillus ustus | − | − | − | − | − | − |
| Aspergillus sp. | − | − | − | − | − | − |
| Beauvaria sp. | − | − | − | − | − | − |
| Bipolaris sp. | − | − | − | − | − | − |
| Blastomyces dermatitidis | − | − | − | − | − | − |
| Candida albicans | − | − | − | − | − | − |
| Candida glabrata | − | − | − | − | + | − |
| Candida guilliermondii | − | − | − | − | − | + |
| Candida kefyr | − | − | − | − | − | − |
| Candida krusei | − | − | − | − | − | − |
| Candida lusitaniae | − | − | − | − | − | − |
| Candida parapsilosis | − | − | − | − | − | − |
| Candida tropicalis | − | − | − | − | − | − |
| Chrysosporium sp. | − | − | − | − | − | − |
| Cladosporium sp. | − | − | − | − | − | − |
| Coccidioides immitis | − | − | − | − | − | − |
| Cryptococcus neoformans | − | − | − | − | − | − |
| Curvularia sp. | − | − | − | − | − | − |
| Fusarium sp. | − | − | − | − | − | − |
| Geotrichum sp. | − | − | − | − | − | − |
| Histoplasma capsulatum | + | − | − | − | − | − |
| Mucor sp. | − | − | − | − | − | − |
| Penicillium sp. | − | − | − | − | − | − |
| P. brasiliensis | − | − | − | − | − | − |
| Pneumocystis carinii | − | − | − | − | − | − |
| Pseudallescheria boydii | − | − | − | − | − | − |
| Rhizopus sp. | − | − | − | − | − | − |
| Saccharomyces cerevisiae | − | − | − | − | − | − |
| Scopulariopsis brevicaulis | − | − | − | − | − | − |
| Sporpthrix schenckii | − | − | − | − | − | − |
| Trichosporon beigelii | − | − | − | − | − | − |

+ Positive
− Negative after 20 minute wash in 2X SSC

TABLE 6

Detection of species specific 28S sequence with probes SEQ ID NO: 15 to SEQ ID NO: 20

| FUNGUS | SEQ ID: 15 | SEQ ID: 16 | SEQ ID: 17 | SEQ ID: 18 | SEQ ID: 19 | SEQ ID: 20 |
|---|---|---|---|---|---|---|
| Acremonium sp. | − | − | − | − | − | − |
| Aspergillus clavatus | − | − | − | − | − | − |
| Aspergillus flavus | − | − | − | − | − | − |
| Aspergillus fumigatus | − | − | − | − | − | − |
| Aspergillus glaucus | − | − | − | − | − | − |
| Aspergillus nidulans | − | − | − | − | − | − |
| Aspergillus niger | − | − | − | − | − | − |
| Aspergillus ochraceus | − | − | − | − | − | − |
| Aspergillus terreus | − | − | − | − | − | − |
| Aspergillus unguis | − | − | − | − | − | − |
| Aspergillus ustus | − | − | − | − | − | − |
| Aspergillus sp. | − | − | − | − | − | − |
| Beauvaria sp. | − | − | − | − | − | − |
| Bipolaris sp. | − | − | − | − | − | − |
| Blastomyces dermatitidis | − | − | − | − | − | − |
| Candida albicans | − | − | − | − | − | − |
| Candida glabrata | − | − | − | − | − | − |
| Candida guilliermondii | − | − | − | − | − | − |
| Candida kefyr | + | − | − | − | − | − |
| Candida krusei | − | + | − | − | − | − |

TABLE 6-continued

Detection of species specific 28S sequence with probes SEQ ID NO: 15 to SEQ ID NO: 20

| FUNGUS | SEQ ID: 15 | SEQ ID: 16 | SEQ ID: 17 | SEQ ID: 18 | SEQ ID: 19 | SEQ ID: 20 |
|---|---|---|---|---|---|---|
| *Candida lusitaniae* | − | − | + | − | − | − |
| *Candida parapsilosis* | − | − | − | + | − | − |
| *Candida tropicalis* | − | − | − | − | + | − |
| Chrysosporium sp. | − | − | − | − | − | − |
| Cladosporium sp. | − | − | − | − | − | − |
| *Coccidioides immitis* | − | − | − | − | − | − |
| *Cryptococcus neoformans* | − | − | − | − | − | − |
| Curvularia sp. | − | − | − | − | − | − |
| Fusarium sp. | − | − | − | − | − | − |
| Geotrichum sp. | − | − | − | − | − | − |
| *Histoplasma capsulatum* | − | − | − | − | − | − |
| Mucor sp. | − | − | − | − | − | − |
| Penicillium sp. | − | − | − | − | − | − |
| *P. brasiliensis* | − | − | − | − | − | − |
| *Pneumocystis carinii* | − | − | − | − | − | − |
| *Pseudallescheria boydii* | − | − | − | − | − | + |
| Rhizopus sp. | − | − | − | − | − | − |
| *Saccharomyces cerevisiae* | − | − | − | − | − | − |
| *Scopulariopsis brevicaulis* | − | − | − | − | − | − |
| *Sporothrix schenckii* | − | − | − | − | − | − |
| *Trichosporon beigelii* | − | − | − | − | − | − |

+ Positive
− Negative after 20 minute wash in 2X SSC

TABLE 7

Detection of species specific 28S sequence with probes SEQ ID NO: 21 to SEQ ID NO: 23

| FUNGUS | SEQ ID: 21 | SEQ ID: 22 | SEQ ID: 23 |
|---|---|---|---|
| Acremonium sp. | − | − | − |
| *Aspergillus clavatus* | − | − | − |
| *Aspergillus flavus* | + | − | − |
| *Aspergillus fumigatus* | − | − | − |
| *Aspergillus glaucus* | − | − | − |
| *Aspergillus nidulans* | − | − | − |
| *Aspergillus niger* | − | − | − |
| *Aspergillus ochraceus* | − | − | − |
| *Aspergillus terreus* | − | − | − |
| *Aspergillus unguis* | − | − | − |
| *Aspergillus ustus* | − | − | − |
| Aspergillus sp | − | − | − |
| Beauvaria sp. | − | − | − |
| Bipolaris sp. | − | − | − |
| *Blastomyces dermatitidis* | − | − | − |
| *Candida albicans* | − | − | − |
| *Candida glabrata* | − | − | − |
| *Candida guilliermondii* | − | − | − |
| *Candida kefyr* | − | − | − |
| *Candida krusei* | − | − | − |
| *Candida lusitaniae* | − | − | − |
| *Candida parapsilosis* | − | − | − |
| *Candida tropicalis* | − | − | − |
| Chrysosporium sp. | − | − | − |
| Cladosporium sp. | − | − | − |
| *Coccidioides immitis* | − | − | − |
| *Cryptococcus neoformans* | − | − | − |
| Curvularia sp. | − | − | − |
| Fusarium sp. | − | − | − |
| Geotrichum sp. | − | − | − |
| *Histoplasma capsulatum* | − | − | − |
| Mucor sp. | − | − | − |
| Penicillium sp. | − | − | − |
| *Paracoccidioides brasiliensis* | − | − | − |
| *Pneumocystis carinii* | − | − | − |
| *Pseudallescheria boydii* | − | − | − |
| Rhizopus sp. | − | − | − |
| *Saccharomyces cerevisiae* | − | − | − |
| *Scopulariopsis brevicaulis* | − | − | − |
| *Sporothrix schenckii* | − | + | + |
| *Trichosporon beigelii* | − | − | − |

+ Positive
− Negative after 20 minute wash in 2X SSC

TABLE 8

Detection of species specific 28S sequence with probes SEQ ID NO: 75 to SEQ ID NO: 76

| FUNGUS | SEQ ID NO: 75 | SEQ ID NO: 76 |
|---|---|---|
| Acremonium sp. | − | − |
| *Aspergillus clavatus* | − | − |
| *Aspergillus flavus* | − | − |
| *Aspergillus fumigatus* | − | − |
| *Aspergillus glaucus* | − | − |
| *Aspergillus nidulans* | − | − |
| *Aspergillus niger* | − | − |
| *Aspergillus ochraceus* | − | − |
| *Aspergillus terreus* | − | − |
| *Aspergillus unguis* | − | − |
| *Aspergillus ustus* | − | − |
| Beauvaria sp. | − | − |
| Bipolaris sp. | − | − |
| *Blastomyces dermatitidis* | − | − |
| *Blasotschizomyces capitatus* | − | − |
| *Candida albicans* | − | − |
| *Candida glabrata* | − | − |
| *Candida guilliermondii* | − | − |
| *Candida krusei* | − | − |
| *Candida lusitaniae* | − | − |
| *Candida parapsilosis* | − | − |
| *Candida tropicalis* | − | − |
| Chrysosporium sp. | − | − |
| Cladosporium sp. | − | − |
| *Coccidioides immitis* | − | − |

TABLE 8-continued

Detection of species specific 28S sequence with probes SEQ ID NO: 75 to SEQ ID NO: 76

| FUNGUS | SEQ ID NO: 75 | SEQ ID NO: 76 |
|---|---|---|
| *Cryptococcus laurentii* | − | − |
| *Cryptococcus neoformans* | − | − |
| var *neoformans* (sero A) | − | − |
| var *neoformans* (sero D) | − | − |
| var *gatti* (sero B) | − | − |
| *Cryptococcus terreus* | − | − |
| Curvularia sp. | − | − |
| *Filobasidium capsuligenum* | − | − |
| *Filobasidium uniguttulatum* | − | − |
| Fusarium sp. | − | − |
| Geotrichum sp. | − | − |
| *Histoplasma capsulatum* | − | − |
| *Malbranchea filamentosum* | − | − |
| Mucor sp. | − | − |
| Paecilomyces sp. | − | − |
| *Paracoccidioides brasiliensis* | | |
| isolate no. 135 | + | − |
| isolate no. 262 | + | − |
| isolate no. 265 | + | − |
| isolate no. 927 | + | − |
| isolate no. 9919 | + | − |
| isolate no. 9894 | + | − |
| Prototheca sp. | − | − |
| Penicillium sp. | − | − |
| *Pneumocystis carinii* | | |
| isolate no. Mayo ref. cult. | − | + |
| isolate no. 56 | − | + |
| isolate no. 62 | − | + |
| isolate no. 69 | − | + |
| isolate no. 85 | − | + |
| *Pseudallesheria boydii* | − | − |
| Rhizopus sp. | − | − |
| *Saccharomyces cerevisiae* | − | − |
| *Scopulariopsis brevicaulis* | − | − |
| *Scopulariopsis brumptii* | − | − |
| *Sporothrix schenckii* | − | − |
| *Trichosporon beigelii* | − | − |

TABLE 9

GenBank search results listing genes from other organisms having 100% identity to probes SEQ ID NO: 3 to SEQ ID NO: 23, SEQ ID NO: 75 and SEQ ID NO: 76

| ORGANISM MATCHED | PROBE SEQ ID NO: | ORGANISM MATCHED | GENE MATCHED* (see note below) | ACCESSION NUMBER |
|---|---|---|---|---|
| *Aspergillus fumigatus* | 3 | — | — | — |
| *Blastomyces dermatitidis* | 4 | *Streptomyces verticillus* | bleomycin acetyl transferase | L26955 |
| | 4 | *Giardia muris* | upstream of rRNA genes | X65063, S53320 |
| | 4 | *Aspergillus nidulans* | uric acid-xanthine permease | X71807 |
| | 4 | *Homo sapiens* | T-cell surface glycoprotein | X16996 |
| | 4 | *Homo sapiens* | MIC2 | M16279, M22557, J03841, M22556 |
| *Candida albicans* | 5 | *Candida albicans* | 28S rRNA | L28817 |
| *Coccidioides immitis* | 6 | — | — | — |
| *Cryptococcus neoformans* | 7 | *Cryptococcus neoformans* | 28S rRNA | L14067, L14068, |
| *Cryptococcus neoformans* | 8 | *Cryptococcus neoformans* | 28S rRNA | L14067, L14068, L20964 |
| | 8 | *Escherichia coli* | 0111 cld | Z17241 |
| *Histoplasma capsulatum* | 9 | — | — | — |
| *Aspergillus glaucus* | 10 | *Pseudomonas denitrificans* | cob genes | M62866 |
| *Aspergillus niger* | 11 | — | — | — |
| *Aspergillus terreus* | 12 | Human cytomegalovirus | genome | X17403 |
| | 12 | *Homo sapiens* | GABA receptor | L08485 |
| *Candida glabrata* | 13 | *Homo sapiens* | Class 1 MHC | X03664, X03665 |
| *Candida guilliermondii* | 14 | — | — | — |
| *Candida kefyr* | 15 | — | — | — |

TABLE 9-continued

GenBank search results listing genes from other organisms having 100% identity to probes
SEQ ID NO: 3 to SEQ ID NO: 23, SEQ ID NO: 75 and SEQ ID NO: 76

| | PROBE SEQ ID NO: | ORGANISM MATCHED | GENE MATCHED* (see note below) | ACCESSION NUMBER |
|---|---|---|---|---|
| *Candida krusei* | 16 | *Pseudomonas syringae* | penicillin binding protein | L28837 |
| *Candida lusitaniae* | 17 | Chicken | AK1 | D00251 |
| | 17 | Mouse | IL10 | M84340 |
| *Candida parapsilosis* | 18 | *Polytomella agilis* | beta-2 tubulin | M33373 |
| | 18 | Tobacco chloroplast | genome | Z00044, S54304 |
| | 18 | *Aedes aegypti* | amylase | L03640 |
| | 18 | *Homo sapiens* | chromosome 13q14 | L14473 |
| *Candida tropicalis* | 19 | — | — | — |
| *Pseudallescheria boydii* | 20 | *Drosophila melanogaster* | AcTr66B | X71789 |
| | | Cow | actin2 | D12816 |
| *Aspergillus flavus* | 21 | — | — | — |
| *Sporothrix schenckii* | 22 | — | — | — |
| *Sporothrix schenckii* | 23 | Sulfate reducing bacteria | FMN binding protein | D21804 |
| | 23 | Equine herpesvirus 1 | genome | M86664 |
| *Paracoccidioides brasiliensis* | 75 | European rabbit | BI-1 calcium channel gene | X57476 |
| *Pneumocystis carinii* | 76 | rice | heat shock protein | D1775 |
| | 76 | *C. elegans* | repetetive DNA | X61259 |
| | 76 | *Synechocystis sp.* | genome | D64000 |
| | 76 | *C. elegans* | various cosmids | Z81063, U59749, Z69662, Z49936, U88182, U80931, Z47358, Z81142, Z79602, Z82084, Z70269 |

* Note: As discussed earlier in this document, the presence of sequences similar to probes SEQ ID NO: 3 to SEQ ID NO: 23, SEQ ID NO: 75 and SEQ ID NO: 76 in genes not related to 28S does not have any effect on the specificity or sensitivity of our diagnostic strategy. Our species specific probes are used to analyze 28S DNA that has been previously amplified in a polymerase chain reaction with our probes SEQ ID NO: 1 and SEQ ID NO: 2. These two probes will not amplify DNA from any gene other than 28S in column #4 (GENE MATCHED), and therefore no amplified DNA from these non-28S genes will be available for the hybridization of probes SEQ ID NO: 3 to SEQ ID NO: 23, SEQ ID NO: 75 and SEQ ID NO: 76.

EXAMPLE 2

Use of method in example 1 to test clinical specimens for specific fungal organisms Clinical samples taken from the respiratory and gastrointestinal tract of healthy individuals almost always contain some fungal flora. Most of these fungi are non-pathogenic, but may give false positives on traditional immunochemical diagnostic tests for pathogenic fungi.

We obtained 44 clinical specimens from diverse sources ranging from sputum and incision drainage tubes, to intervertebral disc and lung biopsies. Traditional smear and culture results showed that all 44 specimens contained at least 1 type of fungus. In order to test the efficacy of our probes, we extracted DNA from all 44 clinical samples and used probes SEQ ID NO: 1 & 2 in a polymerase chain reaction to amplify fungal 28S sequences present in these samples.

DNA was extracted from all clinical samples by our modification of the technique of Chomczynski and Sacchi which originally described the use of acid guanidinium thiocyanate-phenol-chloroform to preferentially extract RNA from cells and tissues. We replaced room temperature cell lysis by boiling lysis, and acid guanidinium thiocyanate-phenol-chloroform extraction by alkaline phenol-guanidine thiocyanate to preferentially extract DNA from cells. 1.5 ml Sarsted (Newton, N.C.) polypropylene screw cap tubes with o-ring seals were used for the extractions. 200 ul of specimen was added to 500 ul of GPT reagent (6 M guanidine thiocyanate dissolved in 50 mM tris pH 8.3 mixed with an equal volume of phenol buffered in tris pH 8.0). This was mixed by vortexing and immediately placed in a boiling water bath for 15 minutes. The tubes were spun in a microcentrifuge for 5 seconds and 250 ul of chloroform/iso-amyl alcohol (24:1 by volume) was added and mixed by vortexing. The liquid phases were separated by centrifugation for 10 minutes and 450 ul of aqueous (upper) phase was transferred to a fresh tube. The aqueous phase was mixed with 500 ul of 100% isopropanol and placed at −20° C. for at least 1 hour. At the end of this period the tubes were centrifuged for 15 minutes and the supernatant removed without disturbing the nucleic acid pellet. The pellet was washed with 500 ul of ice-cold 70% ethanol to remove traces of GPT reagent by gently inverting 2 times and then cen trifuged for 5 minutes. The ethanol was removed and the pellet dried in a speed vac for 10 minutes. The pellet was resuspended in 25 ul of sterile deionized water and 5 ul was used in a 50 ul PCR amplification. The PCR was carried out as a hot-start reaction using the thermal cycling conditions for probes SEQ ID NO: 1 and SEQ ID NO: 2 described in example 1. Gel electrophoresis showed that probes SEQ ID NO: 1 and SEQ ID NO: 2 successfully amplified DNA from all 44 specimens.

The amplified DNA from each specimen was transferred to a positively charged polysulphone based membrane. We radioactively labeled our species specific probes SEQ ID NO: 3, SEQ ID NO: 5, SEQ ID NO: 6 and SEQ ID NO: 7, and sequentially probed the membrane to test for the presence of 28S rDNA from *Aspergillus fumigatus, Candida albicans, Coccidioides immitis* and *Cryptococcus neoformans* respectively. Membrane blocking, probe hybridization and washes were done exactly as described in Example 1. The results are shown in Table 10.

No false positives were observed, indicating a specificity of 100% for these 4 probes in the clinical specimens tested. 10 out of 12 culture positive samples for *Aspergillus fumigatus,* and 11 out of 13 samples of *Candida albicans* were identified, indicating a detection sensitivity of about 85% for these two probes. Additionally, two out of two *Coccidioides immitis* and two out of two *Cryptococcus neoformans* were correctly identified (detection sensitivity of 100%). As seen by these results, the probes described in this invention can be used on a diverse variety of clinical specimens with excellent efficacy.

TABLE 10

Detection of *Aspergillus tumigatus, Candida albicans, Coccidioides immitis* and *Cryptococcus neoformans* in clinical specimens using species specific probes.

| Specimen type | Smear and culture results | PCR with SEQ ID: 1, 2 | SEQ ID: 3 | SEQ ID: 5 | SEQ ID: 6 | SEQ ID: 7 |
|---|---|---|---|---|---|---|
| U035 sputum | *A. flavus* | + | − | − | − | − |
| U069 pleura | *A. tumigatus* | + | + | − | − | − |
| U070 bronchial wash | *A. flavus* | + | − | − | − | − |
| M019 bronchial wash | *A. tumigatus* | + | + | − | − | − |
| M020 sputum | mixed fungal flora | + | − | + | − | − |
| X35254 sputum | *C. albicans* | + | − | + | − | − |
| M20910 sputum | *A. tumigatus* | + | + | − | − | − |
| M055 sputum | *C. albicans* | + | − | + | − | − |
| M056 abdominal | mixed tungal flora | + | − | − | − | − |
| M057 drainage tube | *C. albicans* | + | − | (−) | − | − |
| M059 ind. sputum | *C. albicans* | + | − | + | − | − |
| M060 ind. sputum | mixed tungal flora | + | − | − | − | − |
| M083 bronchial wash | *C. albicans* | + | − | + | − | − |
| M084 sputum | *A. tumigatus* | + | (−) | − | − | − |
| M085 throat | *C. albicans* | + | − | (−) | − | − |
| A001 sputum | *A. tumigatus* | + | (−) | − | − | − |
| A002 leg | Blastomyces | + | − | − | − | − |
| A003 leg | Blastomyces | + | − | − | − | − |
| A005 disc | *A. tumigatus* | + | + | − | − | − |
| A037 disc | *A. tumigatus* | + | + | − | − | − |
| A039 trachea | *C. albicans* | + | − | + | − | − |
| A040 trachea | *C. albicans* | + | − | + | − | − |
| A102 empyema | *A. tumigatus* | + | + | − | − | − |
| Y004 sputum | *C. albicans* | + | − | + | − | − |
| Y016 induced sputum | Coccidioides | + | − | − | + | − |
| Y028 sputum | Coccidioides | + | − | − | + | − |
| J003 chest | Aspergillus sp. | + | − | − | − | − |
| J045 bronchial wash | *C. albicans* | + | − | + | − | − |
| J046 ethmoid | yeast | + | − | − | − | − |
| J047 chest | *A. tumigatus* | + | + | − | − | − |
| J048 sputum | *C. albicans* | + | − | + | − | − |
| J073 lung | Aspergillus sp. | + | − | − | − | − |
| J074 lung | *A. tumigatus* | + | + | − | − | − |
| U017 lip | *A. tumigatus* | + | + | − | − | − |
| U033 sputum | mixed tungal flora | + | − | − | − | − |
| U071 sputum | *C. albicans* | + | − | + | − | − |
| U072 BA lavage | Sporothrix | + | − | − | − | − |
| U073 knee | Histoplasma | + | − | − | − | − |
| U074 mandible | Cryptococcus | + | − | − | − | + |
| U075 CSF | Cryptococcus | + | − | − | − | + |
| U076 knee | Histoplasma | + | − | − | − | − |
| U077 soft tissue | Histoplasma | + | − | − | − | − |
| U051 buccal | *A. tumigatus* | + | + | − | − | − |
| Y055 sputum | mixed tungal flora | + | − | − | − | − |

+ Positive
− Negative
(−) Missed

EXAMPLE 3

DNA sequence based identification of unknown fungal organisms

Another utility of our probes is in the rapid DNA sequence based identification of a pure culture of fungus. Probes SEQ ID NO: 1 and SEQ ID NO: 2 are used in a polymerase chain reaction to amplify 28S rDNA from an unknown fungus. Probes SEQ ID NO: 1 or SEQ ID NO: 2 are then used as sequencing primers to obtain DNA sequence from this amplified 28S DNA belonging to the unknown fungus. This DNA sequence is compared to the fungal 28S DNA sequences in our database, and a sequence match at, or overlapping any one of the probe sequences in SEQ ID NO: 3 to SEQ ID NO: 78 will confirm the identity of the fungus. This technique cannot be used directly on clinical samples, as these usually contain DNA from more than one fungus, and the DNA sequence generated will consist of overlapping sequences of several organisms. This technique has utility in rapidly and reliably identifying colonies of a single fungus on culture plates, clinical specimens, food, pharmaceutical, environmental or other samples containing only one species of fungus.

EXAMPLE 4

Capture and identification of target DNA or RNA

All primers and probes described in this invention disclosure may be labeled with any detectable reporter or signal moiety including, but not limited to radioisotopes, enzymes, antigens, antibodies, chemiluminescent reagents and fluorescent chemicals. Additionally, these probes may be modified without changing the substance of their purpose by terminal addition of nucleotides designed to incorporate restriction sites or other useful sequences. These probes may also be modified by the addition of a capture moiety (including, but not limited to para-magnetic particles, biotin, fluorescein, dioxigenin, antigens, antibodies) or attached to the walls of microtiter trays to assist in the solid phase capture and purification of these probes and any DNA or RNA hybridized to these probes. Fluorescein may be used as a signal moiety as well as a capture moiety, the latter by interacting with an anti-fluorescein antibody.

A typical utility of these modifications would be as follows. Primers SEQ ID NO: 1 and SEQ ID NO: 2 would be utilized to amplify 28S rDNA from a sample, if present, as described previously. Primers would be modified so as to contain a biotin moiety at their 5' ends. A streptavidin solid phase, such as a paramagnetic particle, would be used to separate PCR products, if present, from the reaction mixture. The amplified target may be subsequently hybridized to a third probe ((SEQ ID NO: 3) to (SEQ ID NO: 78) or their complements) attached to a detectable moiety to determine which species of fungus is present in the given sample. Multiple probes, each labeled with a different detectable moiety may be used at one time to analyze the amplified target.

Alternatively, Primers SEQ ID NO: 1 and SEQ ID NO: 2 would be utilized to amplify 28S rDNA from a sample, if present, as above. In a separate reaction, individually, either SEQ ID NO: 1 or SEQ ID NO: 2 would be modified by attachment to a solid phase capture moiety, such as a paramagnetic particle, and SEQ ID NO: 3 to SEQ ID NO: 78 (or their complements) would be modified by addition of a detectable moiety. Alternately, in the amplicon, any sequences delimited by SEQ ID NO: 1 and SEQ ID NO: 2, including but not limited to SEQ ID NO: 3 to SEQ ID NO: 78, may be used in the design of a capture probe. One of the probes attached to a solid phase (SEQ ID NO: 1 and SEQ ID NO: 2) or any other appropriately designed sequences and one of the probes modified by attachment to a detectable moiety (SEQ ID NO: 3 to SEQ ID NO: 78 or their complements) would be hybridized together, in solution, to products of the PCR, if they had been generated. The hybrids, if present, would be captured from the solution, and analyzed by a method appropriate to the detection moiety. Detection of the hybridized probe would indicate which species of fungus was present in the given sample. Multiple probes, each labeled with a different detectable moiety may be used at one time to analyze the amplified target.

EXAMPLE 5

Species-specific amplification of fungal DNA

Another utility of the probes described in this invention is their usage as primers in the direct detection of a specific fungal species by virtue of a nucleic acid amplification reaction. In this embodiment, one primer is a universal one, such as (SEQ ID NO: 1) or (SEQ ID NO: 2), and the other is a species-specific primer selected from the group consisting of (SEQ ID NO: 3) to (SEQ ID NO: 23), (SEQ ID NO: 75) and (SEQ ID NO: 76) or the complements thereof. One variation of this approach is the substitution of (SEQ ID NO: 1) or (SEQ ID NO: 2) with any functional sequence located in proximity to the species-specific primer. Another variation of this approach is the selection of any appropriate species specific primer pair from SEQ ID NO: 24 to SEQ ID NO: 74, SEQ ID NO: 77 and SEQ ID NO: 78.

---

We claim:

1. An oligonucleotide fungal species specific hybridization probe for *Paracoccidioides brasiliensis,* said probe having the nucleotide residue sequence of (SEQ ID NO: 75) or the complement thereof.

2. An oligonucleotide fungal species specific hybridization probe for Pneumocystis carinii, said probe having the nucleotide residue sequence of (SEQ ID NO: 76) or the complement thereof.

3. A method of determining whether one or more fungal species selected from the group of fungal species consisting of *Paracoccidioides brasiliensis* and *Pneumocystis carinii* is present in a sample of fungi, said method comprising the following steps:

a) extracting nucleic acid material from fungi contained in said sample;

b) adding two known oligonucleotide primers, one of said primers being (SEQ ID NO: 1), said primers bracketing a hypervariable region on the 28S rDNA or rRNA present in the fungal species of said group;

c) amplifying the sequence between said primers; and d) using one or more labeled probes directed to a portion of the hypervariable region bracketed by said primers, each said labeled probe being specific for one of said fungal species from said group, to determine whether said fungal species identified by each said labeled probe is present in said sample.

4. The method of claim 3 in which, in said amplifying step, said amplifying procedure is the polymerase chain reaction.

5. The method of claim 3 in which said one or more probes is selected from the group consisting of (SEQ ID NO: 75) and (SEQ ID NO: 76).

6. The method of claim 3 wherein, in step (d), more than one probe is used, each said probe being connected to (a) a different signal moiety or (b) a moiety which allows separation of said probes.

7. A method of determining whether one or more fungal species selected from the group of fungal species consisting of *Paracoccidioides brasiliensis* and *Pneumocystis carinii* is present in a sample of fungi, said method comprising the following steps:

a) extracting nucleic acid material from fungi contained in said sample;

b) adding a universal fungal probe selected from the group consisting of (SEQ ID NO: 1), and the complements thereof;

c) using one or more second probes, each said second probe being specific for one of said fungal species from said group, wherein said one or more second probes each has a nucleotide residue sequence selected from the group consisting of (SEQ ID NO: 75), (SEQ ID NO:76) and the complements thereof; and d) determining whether said fungal species identified by each said second probe is present in said sample, wherein at least one of said probes is connected to a signal moiety and at least one of said probes is connected to a moiety that allows separation of said probes.

8. A species specific reference oligonucleotide for *Paracoccidioides brasiliensis* having the nucleotide residue sequence of SEQ ID NO: 77 or the complement thereof.

9. A species specific reference oligonucleotide for *Pneumocystis carinii* having the nucleotide residue sequence of SEQ ID NO: 78 or the complement thereof.

10. A method of determining whether one or more fungal species selected from the group of fungal species consisting of *Paracoccidioides brasiliensis* and *Pneumocystis carinii* is present in a sample of fungi, said method comprising the following steps:

a) extracting nucleic acid material from fungi contained in said sample;

b) adding two known oligonucleotide primers, one of said primers being (SEQ ID NO: 1) or (SEQ ID NO: 2), said primers bracketing a hypervariable region on the 28S rDNA or rRNA present in the fungal species of said group;

c) amplifying the sequence between said primers; and d) using one or more labeled probes directed to a portion of the hypervariable region bracketed by said primers, each said labeled probe being specific for one of said fungal species from said group, wherein each said one or more labeled probes is fully complementary to a species-unique nucleotide sequence in said hypervariable region, to determine whether said fungal species identified by each said labeled probe is present in said sample, wherein, furthermore, said one or more labeled probes each has a nucleotide residue sequence consisting of from 10 to 50 consecutive nucleotide residues from a sequence selected from the group consisting of (SEQ ID NO: 77) and (SEQ ID NO: 78) and the complements thereof.

11. A method of claim 10 in which said amplifying procedure is the polymerase chain reaction.

12. A method of claim 10 wherein more than one third probe is used, each said third probe connected to a different signal moiety or moiety which allows separation of said third probe.

13. A method of determining whether one or more fungal species selected from the group of fungal species consisting of *Paracoccidioides brasiliensis* and *Pneumocystis carinii* is present in a sample of fungi, said method comprising the following steps:

a) extracting the nucleic acid material from the fungi contained in said sample;

b) adding a universal fungal probe selected from the group consisting of (SEQ ID NO: 1), (SEQ ID NO: 2) and the complements thereof;

c) using one or more second probes, each said second probe being specific for one of said fungal species from said group, wherein each said one or more second probes is fully complementary to a species-unique nucleotide sequence in said hypervariable region and wherein, further, said one or more second probes each has a nucleotide residue sequence consisting of from 10 to 50 consecutive nucleotide residues from a sequence selected from the group consisting of (SEQ ID NO: 77) and (SEQ ID NO: 78) and the complements thereof; and d) determining whether said fungal species identified by each said second probe is present in said sample, wherein at least one of said probes is connected to a signal moiety and at least one of said probes is connected to a moiety that allows separation of said probes.

* * * * *

UNITED STATES PATENT AND TRADEMARK OFFICE
CERTIFICATE OF CORRECTION

PATENT NO. : 6,180,339 B1
DATED : January 30, 2001
INVENTOR(S) : Gurpreet S. Sandhu et al.

It is certified that error appears in the above-identified patent and that said Letters Patent is hereby corrected as shown below:

Column 7,
Line 40, "DATP," should read -- dATP, --;

Column 9,
Line 55, "Maibranchea" should read -- Malbranchea --;

Column 19,
Line 56, "fumigarus" should read -- fumigatus --;

Column 21,
Line 37, "DATP," should read -- dATP, --;

Column 24,
Table 4, the row beginning with "Blastomyces dermatitidis" should read as follows:
-- Blastomyces dermatitidis  -  +  -  -  -  --;

Column 27,
Table 7, first column, "Aspergiilus terreus" should read -- Aspergillus terreus --;

Column 32,
Line 66, "then cen" should read -- then centrifuged --;

Column 33,
Line 1, "trifuged for 5 minutes." should read -- for 5 minutes. --;

UNITED STATES PATENT AND TRADEMARK OFFICE
CERTIFICATE OF CORRECTION

PATENT NO. : 6,180,339 B1  
DATED : January 30, 2001  
INVENTOR(S) : Gurpreet S. Sandhu et al.

Page 2 of 3

It is certified that error appears in the above-identified patent and that said Letters Patent is hereby corrected as shown below:

Column 34,
Please replace the entire "TABLE 10" with new TABLE 10 as follows:

Table 10.

Detection of *Aspergillus fumigatus, Candida albicans, Coccidioides immitis* and *Cryptococcus neoformans* in clinical specimens using species specific probes.

| Specimen type | Smear and culture results | PCR with SEQ ID: 1, 2 | SEQ ID: 3 | SEQ ID: 5 | SEQ ID: 6 | SEQ ID: 7 |
|---|---|---|---|---|---|---|
| U035 sputum | A. flavus | + | - | - | - | - |
| U069 pleura | A. fumigatus | + | + | - | - | - |
| U070 bronchial wash | A. flavus | + | - | - | - | - |
| M019 bronchial wash | A. fumigatus | + | + | - | - | - |
| M020 sputum | mixed fungal flora | + | - | + | - | - |
| X35254 sputum | C. albicans | + | - | + | - | - |
| M20910 sputum | A. fumigatus | + | + | - | - | - |
| M055 sputum | C. albicans | + | - | + | - | - |
| M056 abdominal | mixed fungal flora | + | - | - | - | - |
| M057 drainage tube | C. albicans | + | - | (-) | - | - |
| M059 ind. sputum | C. albicans | + | - | + | - | - |
| M060 ind. sputum | mixed fungal flora | + | - | - | - | - |
| M083 bronchial wash | C. albicans | + | - | + | - | - |
| M084 sputum | A. fumigatus | + | (-) | - | - | - |
| M085 throat | C. albicans | + | - | (-) | - | - |
| A001 sputum | A. fumigatus | + | (-) | - | - | - |
| A002 leg | Blastomyces | + | - | - | - | - |
| A003 leg | Blastomyces | + | - | - | - | - |
| A005 disc | A. fumigatus | + | + | - | - | - |
| A037 disc | A. fumigatus | + | + | - | - | - |
| A039 trachea | C. albicans | + | - | + | - | - |
| A040 trachea | C. albicans | + | - | + | - | - |
| A102 empyema | A. fumigatus | + | + | - | - | - |
| Y004 sputum | C. albicans | + | - | + | - | - |
| Y016 induced sputum | Coccidioides | + | - | - | + | - |
| Y028 sputum | Coccidioides | + | - | - | + | - |
| J003 chest | Aspergillus sp. | + | - | - | - | - |
| J045 bronchial wash | C. albicans | + | - | + | - | - |
| J046 ethmoid | yeast | + | - | - | - | - |
| J047 chest | A. fumigatus | + | + | - | - | - |
| J048 sputum | C. albicans | + | - | + | - | - |
| J073 lung | Aspergillus sp. | + | - | - | - | - |
| J074 lung | A. fumigatus | + | + | - | - | - |
| U017 lip | A. fumigatus | + | + | - | - | - |
| U033 sputum | mixed fungal flora | + | - | - | - | - |
| U071 sputum | C. albicans | + | - | + | - | - |
| U072 BA lavage | Sporothrix | + | - | - | - | - |
| U073 knee | Histoplasma | + | - | - | - | - |
| U074 mandible | Cryptococcus | + | - | - | - | + |
| U075 CSF | Cryptococcus | + | - | - | - | + |
| U076 knee | Histoplasma | + | - | - | - | - |
| U077 soft tissue | Histoplasma | + | - | - | - | - |
| U051 buccal | A. fumigatus | + | + | - | - | - |
| Y055 sputum | mixed fungal flora | + | - | - | - | - |
| + Positive  - Negative  (-) Missed | | | | | | | and

UNITED STATES PATENT AND TRADEMARK OFFICE
CERTIFICATE OF CORRECTION

PATENT NO.    : 6,180,339 B1
DATED         : January 30, 2001
INVENTOR(S)   : Gurpreet S. Sandhu et al.

It is certified that error appears in the above-identified patent and that said Letters Patent is hereby corrected as shown below:

<u>Column 87,</u>
Line 29, "ments thereof;" should read -- ment thereof; --

Signed and Sealed this

Third Day of February, 2004

JON W. DUDAS
*Acting Director of the United States Patent and Trademark Office*